(12) United States Patent
Pacheco

(10) Patent No.: US 8,167,884 B2
(45) Date of Patent: May 1, 2012

(54) SYSTEM AND METHODS FOR IMPROVED ACCESS TO VERTEBRAL BODIES FOR KYPHOPLASTY, VERTEBROPLASTY, VERTEBRAL BODY BIOPSY OR SCREW PLACEMENT

(75) Inventor: Hector O. Pacheco, El Paso, TX (US)

(73) Assignee: Leucadia 6, LLC, El Paso, TX (US)

( * ) Notice: Subject to any disclaimer, the term of this patent is extended or adjusted under 35 U.S.C. 154(b) by 870 days.

(21) Appl. No.: 12/230,552

(22) Filed: Aug. 29, 2008

(65) Prior Publication Data

US 2009/0005790 A1    Jan. 1, 2009

Related U.S. Application Data

(62) Division of application No. 11/369,023, filed on Mar. 7, 2006, now Pat. No. 7,623,902.

(60) Provisional application No. 60/658,576, filed on Mar. 7, 2005.

(51) Int. Cl.
*A61F 5/00* (2006.01)
(52) U.S. Cl. .................................... 606/86 A
(58) Field of Classification Search ............... 606/86 A, 606/86 R, 92–96, 104
See application file for complete search history.

(56) References Cited

U.S. PATENT DOCUMENTS

| | | | |
|---|---|---|---|
| 5,291,537 A | 3/1994 | Mazess | |
| 5,351,404 A | 10/1994 | Smith | |
| 5,591,207 A * | 1/1997 | Coleman | 606/232 |
| 5,682,886 A | 11/1997 | Delp | |
| 5,748,767 A | 5/1998 | Raab | |
| 5,772,594 A | 6/1998 | Barrick | |
| 5,799,055 A | 8/1998 | Peshkin | |
| 5,850,836 A | 12/1998 | Steiger | |
| 5,871,018 A | 2/1999 | Delp | |
| 6,002,959 A | 12/1999 | Steiger | |
| 6,048,331 A * | 4/2000 | Tsugita et al. | 604/102.03 |
| 6,069,932 A | 5/2000 | Peshkin | |
| 6,167,296 A | 12/2000 | Shahidi | |
| 6,175,758 B1 | 1/2001 | Kambin | |
| 6,198,794 B1 | 3/2001 | Peshkin | |
| 6,226,548 B1 | 5/2001 | Foley | |
| 6,282,437 B1 | 8/2001 | Franck et al. | |
| 6,351,662 B1 | 2/2002 | Franck et al. | |
| 6,470,207 B1 | 10/2002 | Simon et al. | |
| 6,477,400 B1 | 11/2002 | Barrick | |
| 6,484,044 B1 | 11/2002 | Lilienfeld-Toal | |
| 6,490,467 B1 | 12/2002 | Bucholz et al. | |
| 6,490,475 B1 | 12/2002 | Seeley et al. | |
| 6,529,765 B1 | 3/2003 | Franck et al. | |
| 6,546,277 B1 | 4/2003 | Franck et al. | |
| 6,697,664 B2 | 2/2004 | Kienzle, III et al. | |
| 6,741,883 B2 | 5/2004 | Gildenberg | |
| 7,235,076 B2 | 6/2007 | Pacheco | |
| 7,278,970 B2 * | 10/2007 | Goldenberg | 600/564 |
| 2002/0161368 A1 | 10/2002 | Foley et al. | |
| 2004/0092932 A1 | 5/2004 | Aubin et al. | |
| 2004/0092988 A1* | 5/2004 | Shaolian et al. | 606/167 |
| 2004/0240715 A1 | 12/2004 | Wicket et al. | |

* cited by examiner

*Primary Examiner* — William H Matthews
(74) *Attorney, Agent, or Firm* — Nixon & Vanderhye PC

(57) ABSTRACT

A method for providing access to the interior of a pedicle for a desired transpedicular procedure including the step of positioning a cannula through a drilled opening in the posterior cortex of the pedicle, the cannula having an inner section positioned in the opening and an enlarged outer section extending from the cortex. The outer section having a longitudinal slot which enables an instrument that is straight or angled to be inserted through the slot and into the pedicle for a surgical procedure.

8 Claims, 32 Drawing Sheets

MAXIMUM SIZE PARAMETERS

| Vertebral Pedicle | Diameter (mm) | Length (mm) | Sagittal Trajectory (°) | Transverse Trajectory (°) |
|---|---|---|---|---|
| Lumbar 1 - left | 5.35 | 40 | 10 | 10 |
| Lumbar 1 - Right | 5.56 | 43 | 10 | 15 |
| Lumbar 2 - left | 6.34 | 45 | 10 | 17 |
| Lumbar 2 - Right | 6.34 | 45 | 10 | 22 |
| Lumbar 3 - left | 7.55 | 45 | 15 | 20 |
| Lumbar 3 - Right | 9.23 | 45 | 15 | 23 |
| Lumbar 4 - left | 11.37 | 47 | 10 | 25 |
| Lumbar 4 - Right | 8.53 | 43 | 12 | 30 |
| Etc. | | | | |

MAXIMUM AVAILABLE SCREW SIZE PARAMETERS

| Vertebral Pedicle | Diameter (mm) | Length (mm) | Sagittal Trajectory (°) | Transverse Trajectory (°) | Pedicle Base Circumference Outline (Coronal Trajectory) | Pedicle Distance A - B (mm) |
|---|---|---|---|---|---|---|
| Lumbar 1 - left | 5.00 | 40 | 10 | 10 | | 14 |
| Lumbar 1 - Right | 5.00 | 40 | 10 | 15 | | 16 |
| Lumbar 2 - left | 6.00 | 45 | 10 | 17 | | 17 |
| Lumbar 2 - Right | 6.00 | 45 | 10 | 22 | | 18 |
| Lumbar 3 - left | 7.00 | 45 | 15 | 20 | | 20 |
| Lumbar 3 - Right | 8.00 | 45 | 15 | 23 | | 20 |
| Lumbar 4 - left | 8.00 | 47 | 10 | 25 | | 15 |
| Lumbar 4 - Right | 8.00 | 40 | 12 | 30 | | 19 |
| Etc. | | | | | | |

Fig. 12

LUMBAR

THORACIC

CERVICAL

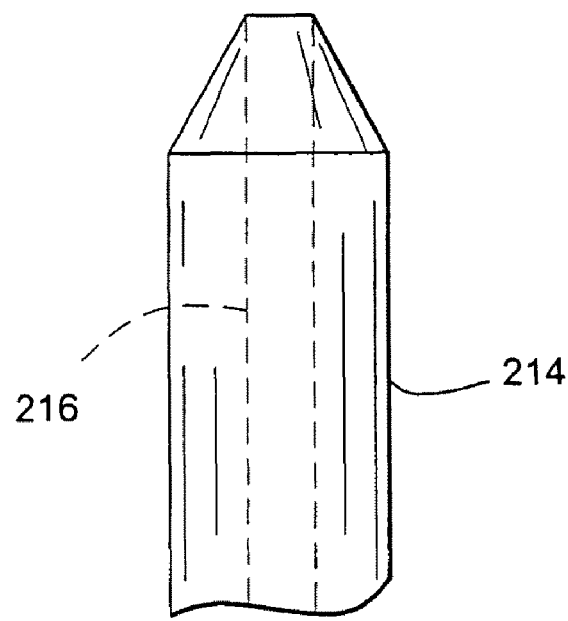
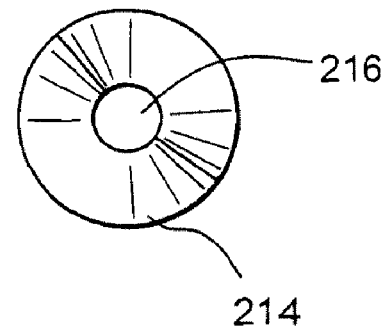
Fig. 21a
Fig. 21b
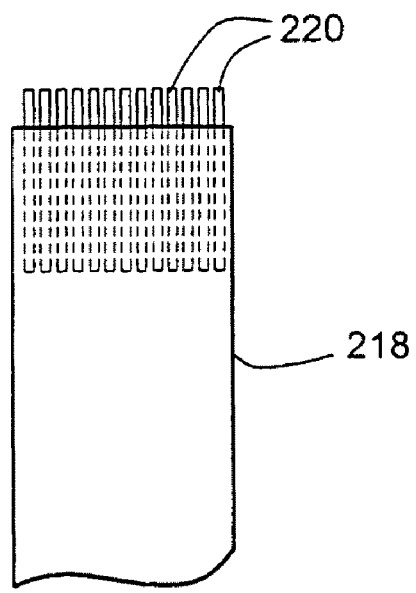
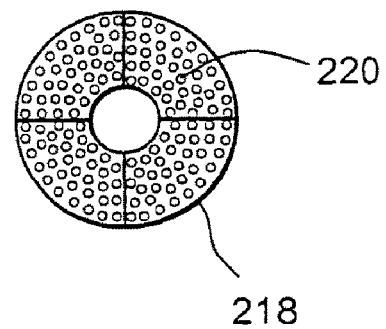
Fig. 22a
Fig. 22b

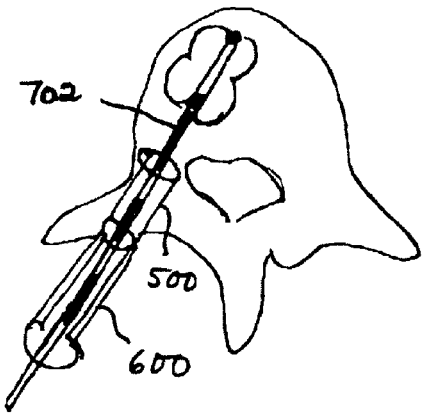
FIG. 37
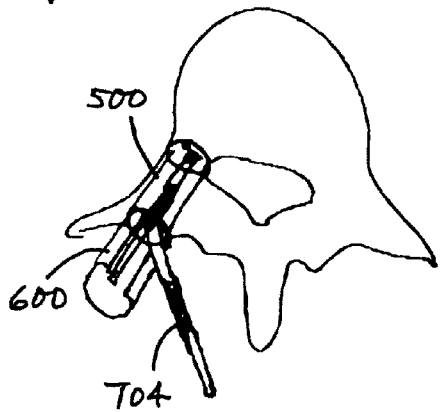 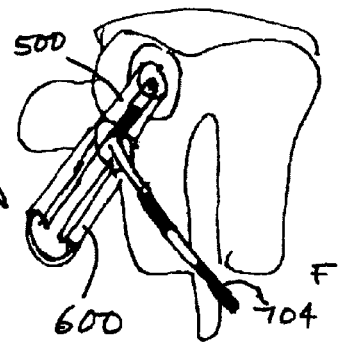
FIG. 38a　　　　　　　　　　　　　FIG. 38b
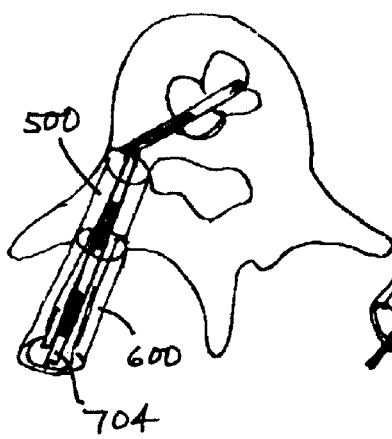 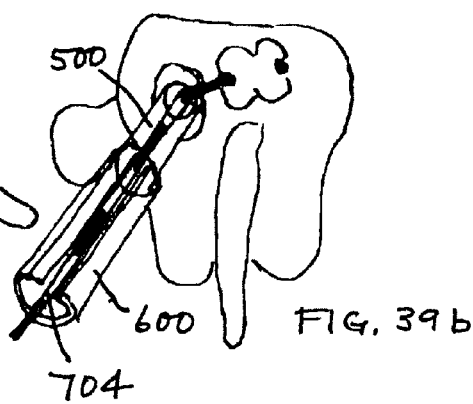
FIG. 39a　　　　　　　　　　　　　FIG. 39b

SYSTEM AND METHODS FOR IMPROVED ACCESS TO VERTEBRAL BODIES FOR KYPHOPLASTY, VERTEBROPLASTY, VERTEBRAL BODY BIOPSY OR SCREW PLACEMENT

CROSS REFERENCE TO RELATED APPLICATION

This is a divisional application of U.S. patent application Ser. No. 11/369,023 filed Mar. 7, 2006 now U.S. Pat. No. 7,623,902, the entirety of which application is incorporated by reference.

FIELD OF THE INVENTION

The present invention relates to the general field of spinal surgery and, more particularly, to a manual, computerized or automated method for the accurate sizing and placement of instruments or screws in pedicles during spinal surgical procedures.

BACKGROUND OF THE INVENTION

Many medical conditions impact on the human spine anatomy. With the growing elderly population there are an increasing number of patients who are sustaining osteopenic or osteoporotic vertebral body compression fractures that creates significant morbidity and/or mortality for them. Traditional methods for dealing with these compression fractures are not always very effective. As a result, methods to strengthen the vertebral body have evolved with significant clinical improvement for affected patients. A common procedure for this is vertebroplasty in which a bone substitute, such as polymethylmethacrylate, hydroxylapatite compound or other material is injected into the vertebral body usually through a transpedicular approach, through the vertebral body pedicle, and sometimes through an extrapedicular approach. An improvement upon the vertebroplasty is the kyphoplasty procedure in which a balloon catheter is introduced usually through a transpedicular approach into the vertebral body and the catheter is then inflated to nearly restore the original vertebral body anatomy. When the catheter is deflated it leaves behind a cavitary void which is then filled with materials similar to the vertebroplasty. Both of these procedures have significant benefit for the patient in that they are usually performed through a percutaneous method which allows for outpatient management. Occasionally, treated patients may need to have an overnight hospital admission.

The use of vertebroplasty and kyphoplasty has extended to include management of vertebral body tumors, traumatic burst fractures and sometimes prophylactic management of impending fractures. A key element of eligible criteria for either procedure has traditionally been that the vertebral body must have an intact posterior vertebral body wall to avoid iatrogenic injury to the spinal cord secondary to leakage of injected material.

To reduce iatrogenic injury a number of safeguards have been instituted. Some of these safeguards include use of a radioopaque contrast material mixed with the injected material to visualize under radiographic imaging (fluoroscopy); performing the procedure in a controlled environment with biplanar fluoroscopic imaging (anterior-posterior and lateral imaging); miniaturization of equipment to prevent pedicle cortical wall breach, bilateral transpedicular approaches to vertebral bodies to maximize volume of injected material; limiting number of vertebral bodies injected at one setting to three or less vertebral bodies; limiting kyphoplasty to vertebral bodies below thoracic level 4 T4; and other strategies.

Inherent to successful outcome of procedures such as vertebroplasty, kyphoplasty, vertebral body biopsy, pedicle screw placement or others is a consistently same and reproducible access to the vertebral body. This access is usually a transpedicular approach, but can also be performed through an extrapedicular approach.

This invention provides a safe and reproducible method to transpedicular and extrapedicular approaches to any vertebral body. Furthermore, it includes specific embodiments to improve current methods of vertebroplasty, kyphoplasty, vertebral body biopsy and pedicle screw placement. This invention reduces radiographic imaging for these procedures to primarily anterior-posterior fluoroscopic visualization and can be utilized in either a percutaneous or open surgical environment with pedicle screw instrumentation present or absent.

The critical parameters for performing any of these procedures are through knowledge of the pedicle diameter, length and trajectory and then actual placement of instruments and/or screws. To date many of the image guided systems allow for manual determination of these parameters and to improve a surgeon's manual performance in these procedures. As of yet, no invention or system is available which will automatically determine ideal pedicle diameter, length, trajectory and actual placement of instruments or screws.

SUMMARY OF THE INVENTION

This invention will automatically generate a table providing the maximum allowable pedicle diameter and length, summary data on trajectory and also generate a schematic diagram illustrating this data for individual vertebral pedicles. The numeral data can be utilized by the surgeon for actual intraosseous transpedicular access by one of five methods: (Method A) manual instrument or screw placement by the surgeon's preferred method. (Method B) utilize pedicle base circumference outline method using a variable length adjustable awl combined with intraoperative fluoroscopy, or (Method C) automated instrument or screw placement using the two ring aligning apparatus and drill guide method or (Method D) with any commercially available computed tomography/fluoroscopy registration software. This invention also allows for extraosseous or extrapedicular pedicle instrument or screw placement (Method E) if a surgeon should so desire based on a trajectory beginning at the same starting point of the anterior cortex but angled tangentially to any distance or angle to surgeon's desired preference. Furthermore, this invention allows trajectory of instrument or screw placement to proceed along a planned eccentric placement that is transpedicular but centered within the pedicle isthmus (Method F).

One method of the present invention generally comprises the following steps:

1. A computed tomography scan (CT), magnetic resonance image (MRI), CT capable fluoroscopy or similar two dimensional imaging study of the spine area of interest may first be obtained.

2. A dimensionally true three dimensional computer image of the bony spine is generated from the CT, MRI or other studies, or in any other suitable manner.

3. The computer generated three dimensional individual vertebra are then hollowed out by a computer or other device similar to an eggshell transpedicular vertebral corpectomy to the specifications desired by the surgeon, e.g., thickness of cortical wall remaining in the vertebral body cortices or pedicle walls. The individual vertebra can be visualized as a structure which has been cored or hollowed out and the resulting remaining vertebral body is highlighted throughout its walls.

4. A computer then automatically determines the maximum allowable instrument or screw diameter to be placed by determining the narrowest diameter or smallest cross sectional area (isthmus) within any given pedicle based on surgeon pedicle cortical wall diameter preferences.

5. A computer, for normal vertebra, then generates an elongated cylinder by starting at the center of the isthmus as a straight line which determines the ideal trajectory and extends in opposite directions e.g., perpendicular to the plane of the isthmus so that it is positioned concentrically as much as possible within the pedicle without touching the remaining highlighted cortex. This line is allowed to penetrate the dorsal or posterior pedicle cortex so that it can extend beyond the skin of a patient to any desired length. The line terminates inside the vertebral body to within a surgeon's predetermined distance from the predefined anterior inner cortical wall so that it cannot penetrate it.

6. A computer, for fractured vertebra, then generates an elongated cylinder by starting at the center of the isthmus as a straight line which projects to the point centered within the anterior vertebral body to determine this ideal trajectory and extends posteriorly without touching the remaining highlighted cortex. This line is allowed to penetrate the dorsal or posterior pedicle cortex so that it can extend beyond the skin of a patient to any desired length. The line terminates inside the vertebral body to within a surgeon's predetermined distance from the predefined anterior inner cortical wall so that it cannot penetrate it.

7. A computer then builds the line concentrically in radial directions to a final maximum diameter which will not exceed the narrowest defined pedicle diameter based on surgeon preference pedicle conical wall thickness. This concentric building grows into a visible cylinder which stops building when any point on its outer surface comes into "contact" with the highlighted inner cortical wall. This rule, however, does not apply to the posterior cortex adjacent to the existing straight trajectory line generated from the isthmus.

8. A computer then determines the length of the screw by measuring the length of the cylinder starting at the pedicle base circumference up to its intersection with the dorsal/posterior cortex.

9. A computer then determines the length of the screw by measuring the length of the cylinder starting at the predefined anterior inner cortex up to its intersection with the dorsal/posterior cortex. To facilitate the placement of instruments or screws in accordance with one of the automated methods described hereinafter, the cylinder may be extended beyond its intersection with the dorsal/posterior cortex.

10. A computer then provides a data summary table which displays the ideal pedicle instrument or screw diameter, length or trajectory for each individual vertebra pedicle and an idealized schematic drawing of same.

11. The tabulated can be utilized to determine the viability of using pedicle instruments or screws based on maximal pedicle instrument or screw diameter and length, and also for placement of instruments or screws by a surgeon's preferred method, such as one of the methods described hereinafter.

BRIEF DESCRIPTION OF THE DRAWINGS

FIG. 10b is a schematic side view of a vertebra showing the sagittal plane and the nature of the trajectory angles in FIG. 10a; and FIG. 10c is a schematic plan view of a vertebra showing the transverse plane and the nature of the trajectory angles in FIG. 10a;

FIG. 10d is a schematic rear view of a vertebra showing the coronal plane and the nature of the trajectory angles in FIG. 10a;

FIG. 12 is a table of maximum available screw size parameters corresponding to the data in the summary table of FIG. 10a and pedicle base circumference outlines (coronal planes) and pedicle distance points A-B;

FIG. 19b is a front elevational view of the apparatus shown in FIG. 19a;

FIGS. 21a and 21b are side and front elevational views of the end portion of a first embodiment of a drilling cannula member for the dual ring aligning apparatus shown in FIGS. 19a and 19b;

FIGS. 22a and 22b are side and front elevational views of the end portion of a second embodiment of a drilling cannula member for the dual ring aligning apparatus shown in FIGS. 19a and 19b;

FIG. 37 is a schematic view similar to FIG. 36 wherein a balloon catheter is inserted in the vertebra through the second and/or first cannulas;

FIGS. 38a and 38b are schematic plan and rear elevation views, respectively, of a vertebra with an angled catheter partially inserted through the second cannula; and FIGS. 39a and 39b are schematic views similar to FIGS. 38a and 38b, respectively, showing the angled catheter fully inserted in the vertebra through the second cannula.

DETAILED DESCRIPTION OF THE INVENTION

The methods of determining pedicle screw size and placement in accordance with the present invention is set forth in more detail hereinafter.

Step 1

A computed tomography scan (CT), magnetic resonance image (MRI), CT capable fluoroscopy or similar two-dimensional imaging study of the spine area of interest may first be obtained. Thin cut sections are preferable to increase accuracy and detail.

Step 2

Figure 1A:
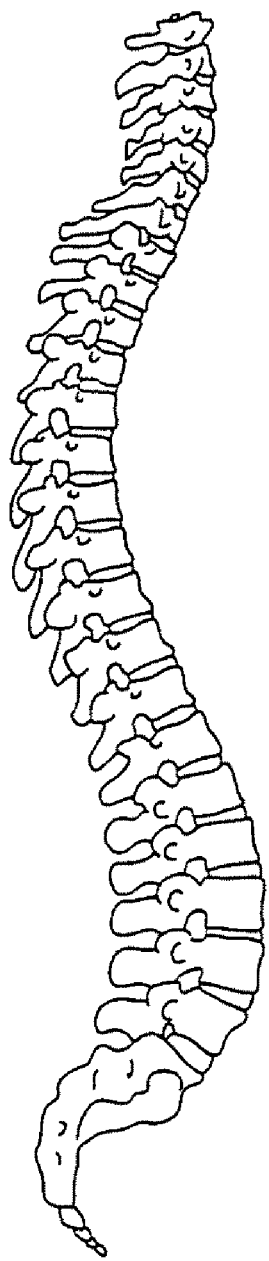
FIGS. 1a and 1b are three dimensional computer images of the side and back, respectively, of the bony spine made from CT, MRI or other studies of the spine area of interest.
Figure 1B:
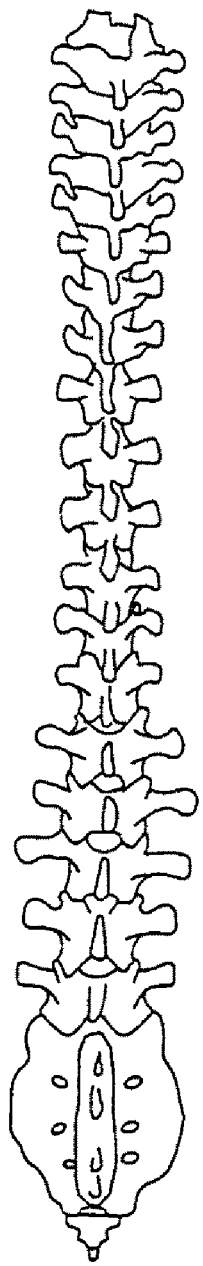

A dimensionally true three dimensional computer image of the bony spine is made from the CT, MRI or other studies or in any other suitable manner, as shown in FIGS. 1a and 1b.

Step 3

Figure 2:
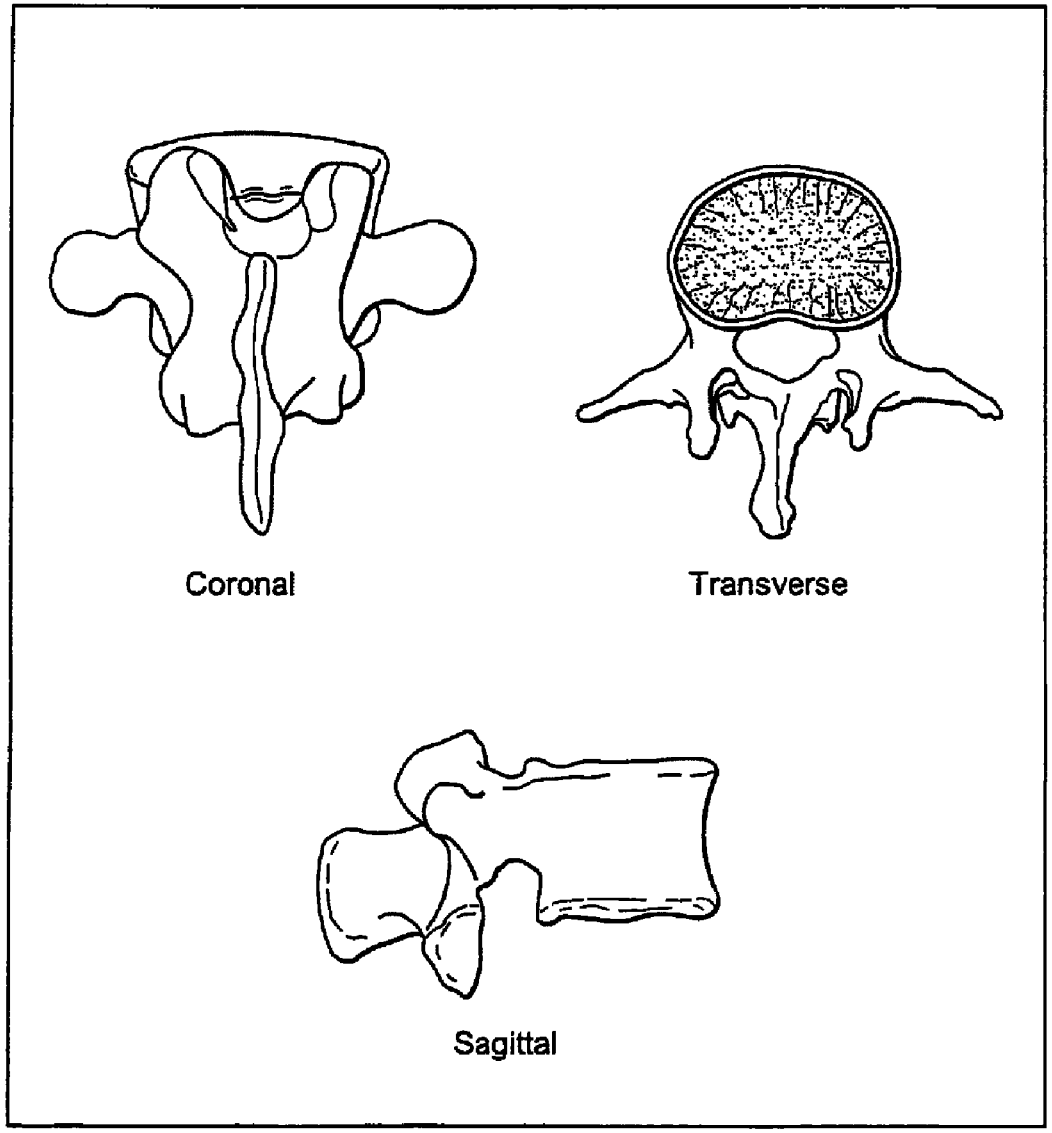
FIG. 2 illustrates three dimensional computer images of individual vertebra undergoing a manual eggshell corpectomy from the spine area shown in FIGS. 1a and 1b.

The three dimensional individual vertebra as shown in FIG. 2 are then hollowed out by a computer, similar to an eggshell transpedicular vertebral corpectomy, to the specifications desired by the surgeon (i.e., thickness of cortical wall remaining in the vertebral body cortices or pedicle walls). These specifications allow for asymmetric thicknesses, such that, for example, anterior vertebral body cortex could be five millimeters thick, lateral vertebral body wall seven millimeters thick and the pedicle walls only one millimeter thick; or body cortical wall uniformly five millimeters thick and pedicle walls only one millimeter thick or the like. The individual vertebra can be visualized as a structure which has been cored or hollowed out and the resulting remaining vertebral body is "electrified" or highlighted in a suitable manner throughout its walls.

Step 4

Figure 3:
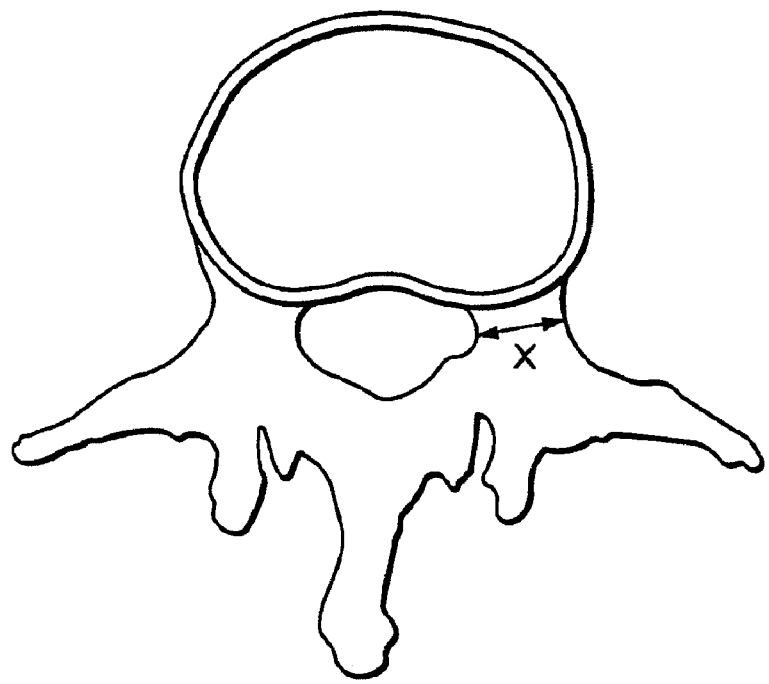
FIG. 3 is a computer image of a hollowed out individual vertebra showing the narrowest diameter or cross sectional area (isthmus) within the pedicle.

A computer then automatically determines the maximum allowable diameter screw to be placed by determining the narrowest diameter or cross sectional area (isthmus) X within any given pedicle based on surgeon pedicle cortical wall diameter preferences, as shown in FIG. 3.

Step 5

A computer then generates an elongated cylinder by starting at the center of the isthmus X as a straight line 10 in FIG.

4 which determines the ideal axis/trajectory and extending in opposite directions, e.g., perpendicular to the plane of the isthmus of the pedicle so that it is positioned concentrically as much as possible within the pedicle without touching the remaining cortex with the center of the isthmus being the fulcrum. This line is allowed to penetrate the dorsal or posterior pedicle cortex so that it can extend beyond the skin of a patient to any desired length. The line terminates inside the vertebral body to within a predetermined distance (e.g. 5 mm) from the predefined anterior inner cortical wall, as selected by the surgeon, so that it does not penetrate the anterior outer cortex and also maximizes screw diameter described hereinafter.

Step 6

Figure 5:
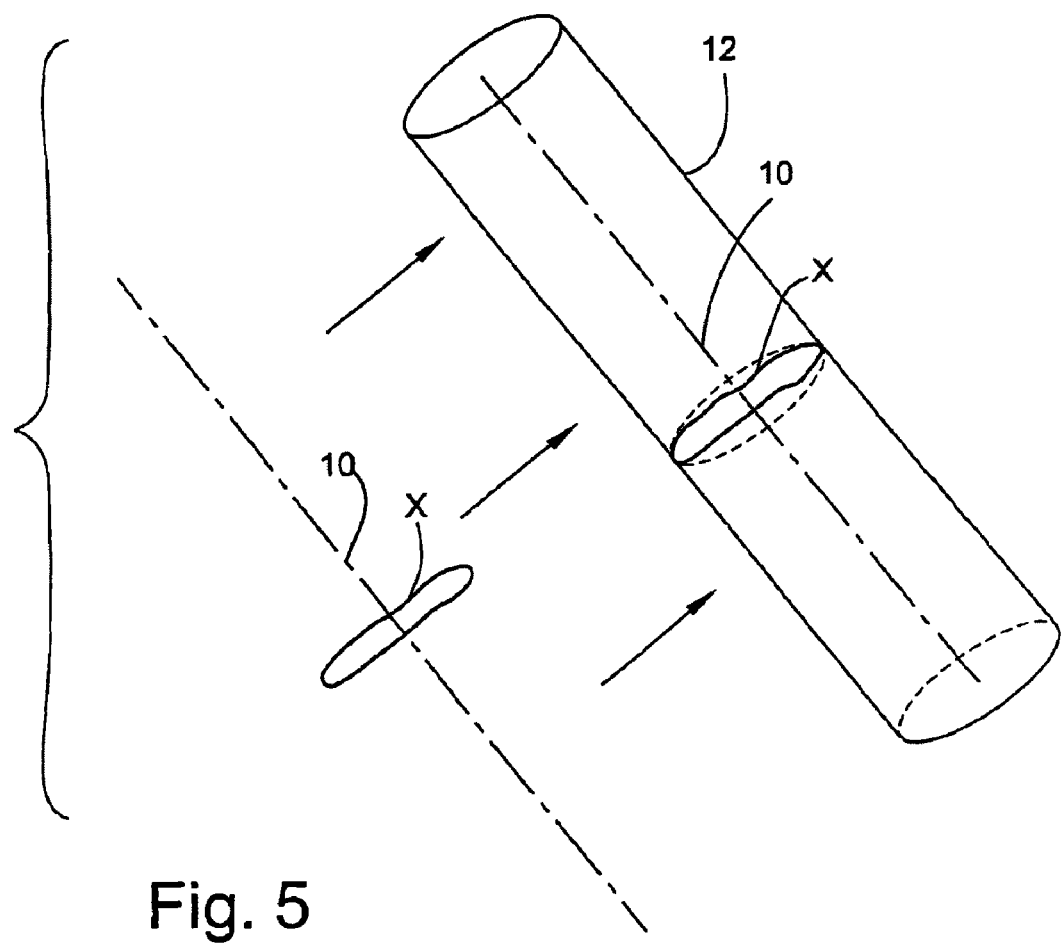
FIG. 5 is a schematic drawing showing the generation of the cylinder by building the line extending through the center of the isthmus concentrically in radial directions.

A computer then builds the line 10 concentrically in radial directions as shown schematically in FIG. 5 to its final maximum diameter which will not exceed the narrowest defined pedicle diameter based on surgeon preference pedicle cortical wall thickness. This concentric building ultimately grows into a visible cylinder 12 which stops building when any point on its outer surface comes into "contact" with the highlighted inner cortical wall. The cylinder formed has at its center the beginning line 10 which may be identified in a different color or pattern than the concentrically built cylinder 12. As described hereinafter, the cylinder 12 may be extended beyond its intersection with the dorsal/posterior cortex to facilitate the placement of screws in accordance with one of the automated methods described hereinafter.

Step 7

Figures 6A, 6B:
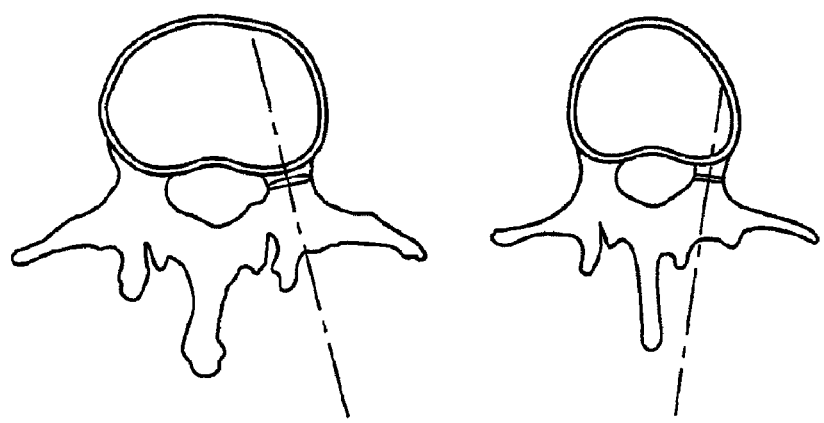
FIGS. 6a and 6b are schematic images of hollowed out individual vertebra that are of symmetrical and irregular shape, respectively.
Figures 7A, 7B:
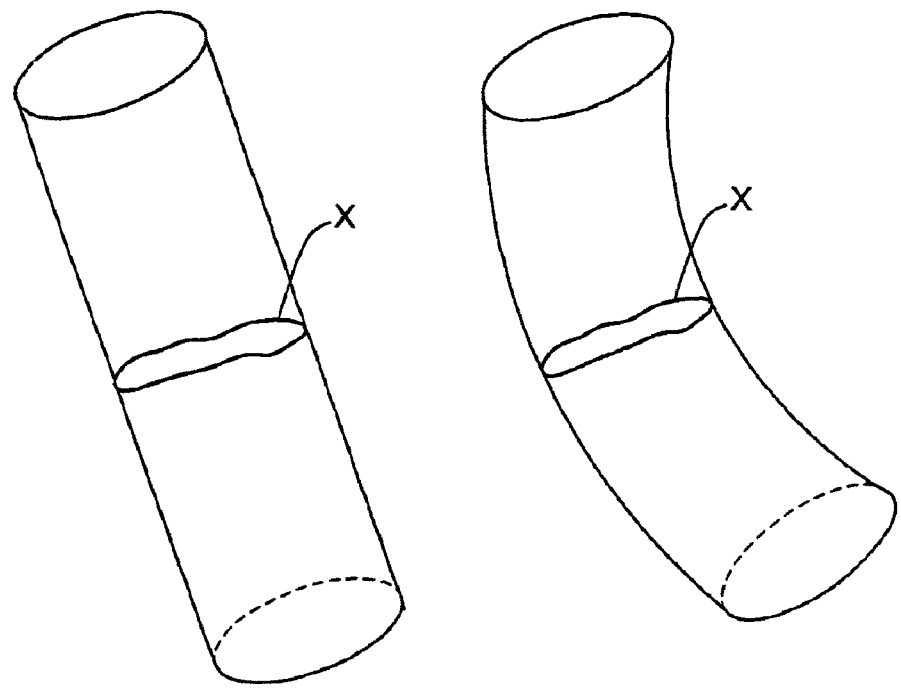
FIGS. 7a and 7b are schematic views showing the isthmus of straight and curved pedicles, respectively.

The maximal diameter allowed may actually be less than that determined by the narrowest diameter method for those pedicles which have irregular anatomy, as shown in FIG. 6b, such as curved pedicles (FIG. 7b) or a similar deformity. This prevents cortical pedicle wall breach.

Step 8

Figure 8:
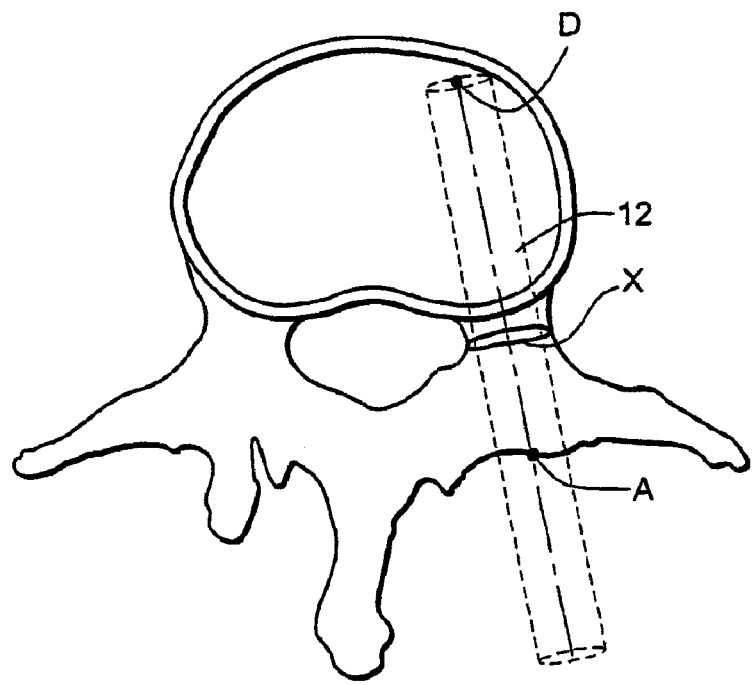
FIG. 8 is a schematic view of a hollowed out vertebra showing the length of the cylinder for determining pedicle screw length.

A computer then determines the length of the screw by measuring the length of the cylinder 12 starting at the point D in FIG. 8 adjacent to the predefined anterior inner cortex up to its intersection A with the dorsal/posterior cortex.

Step 9

Figures 9, 10A:
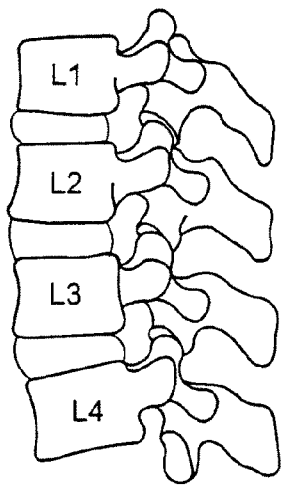
FIG. 9 is a schematic side elevational view of the individual vertebra labeled by a surgeon for pedicle screw installation.
FIG. 10a is a data summary table generated by a computer of maximum pedicle screw diameter and length, and also of the trajectory angle of the pedicle screw with respect to the sagittal and transverse planes.
Figure 10B:
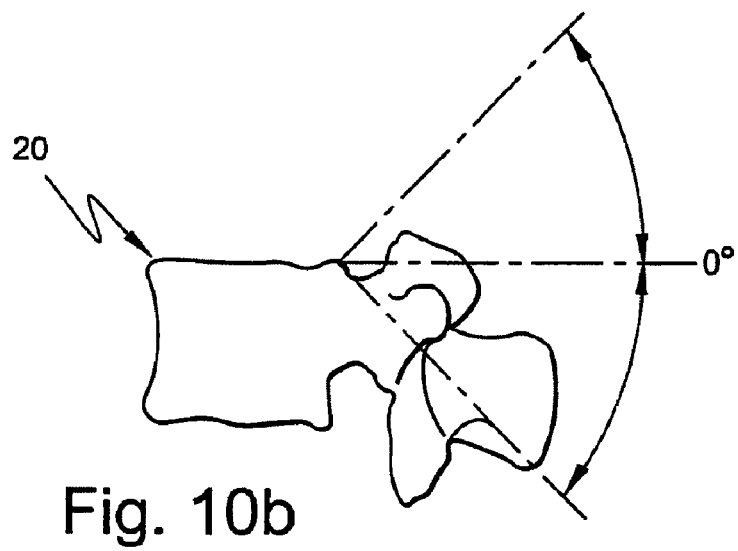
Figure 10C:
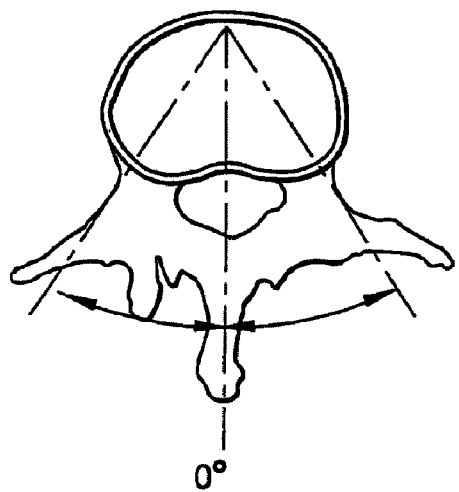
Figure 11:
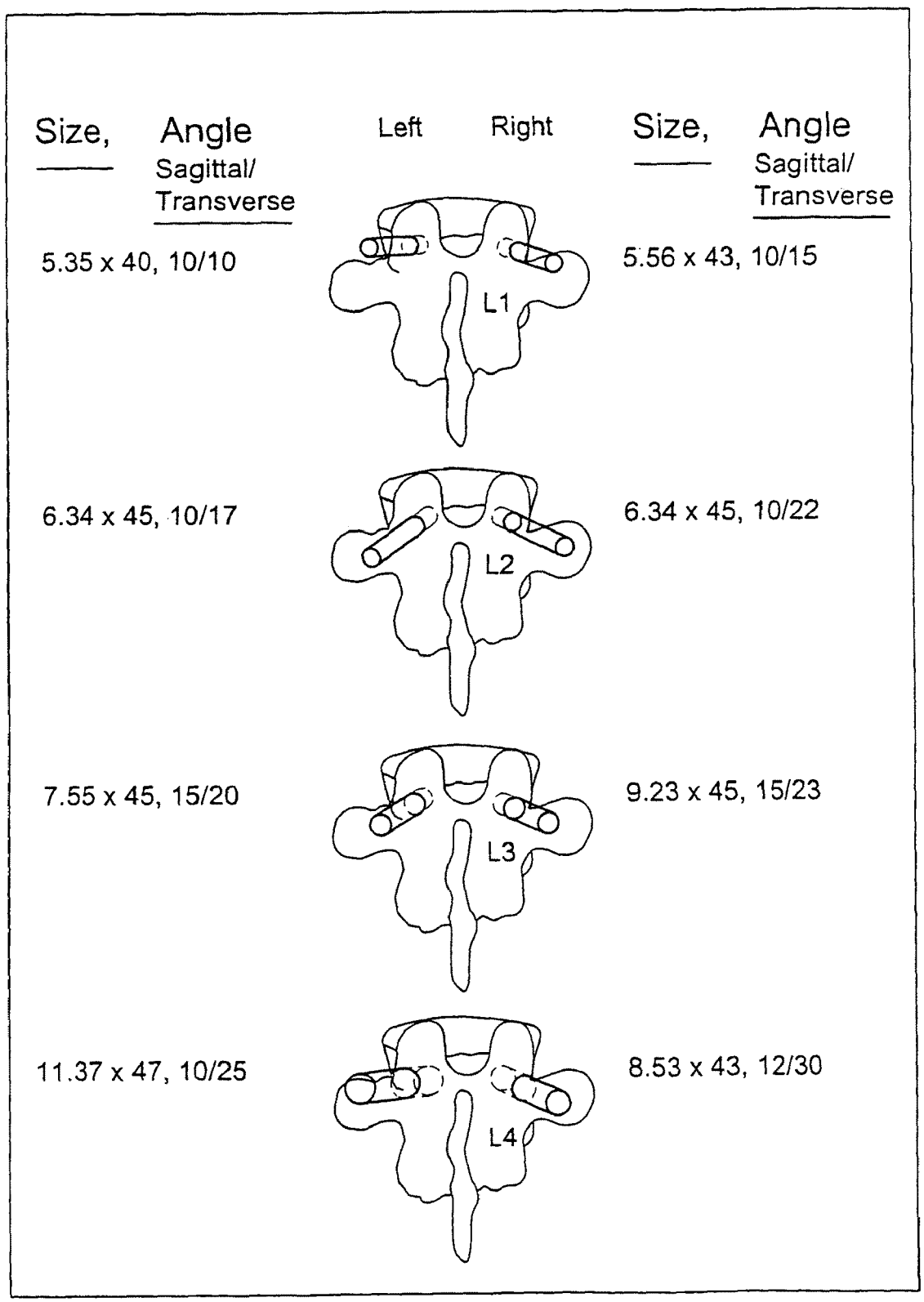
FIG. 11 is a computer generated schematic view of the ideal pedicle screw placements as identified in the data summary table of FIG. 10a in AP plane demonstrating coronal trajectory.

A computer then provides a data summary table as shown in FIG. 10a which displays the ideal pedicle screw diameter, length and trajectory (measured as an angle shown in FIGS. 10b and 10c with respect to the transverse and sagittal planes with corresponding superior end plate as the reference plane) for each individual vertebra pedicle, and also provides idealized schematic drawings as shown in FIG. 11. Individual vertebra are labeled by having the surgeon identify any specific vertebra as shown in FIG. 9 and then the computer automatically labels the remaining vertebral bodies with the surgeon confirming accurate vertebral body labeling.

Step 10

Figure 13:
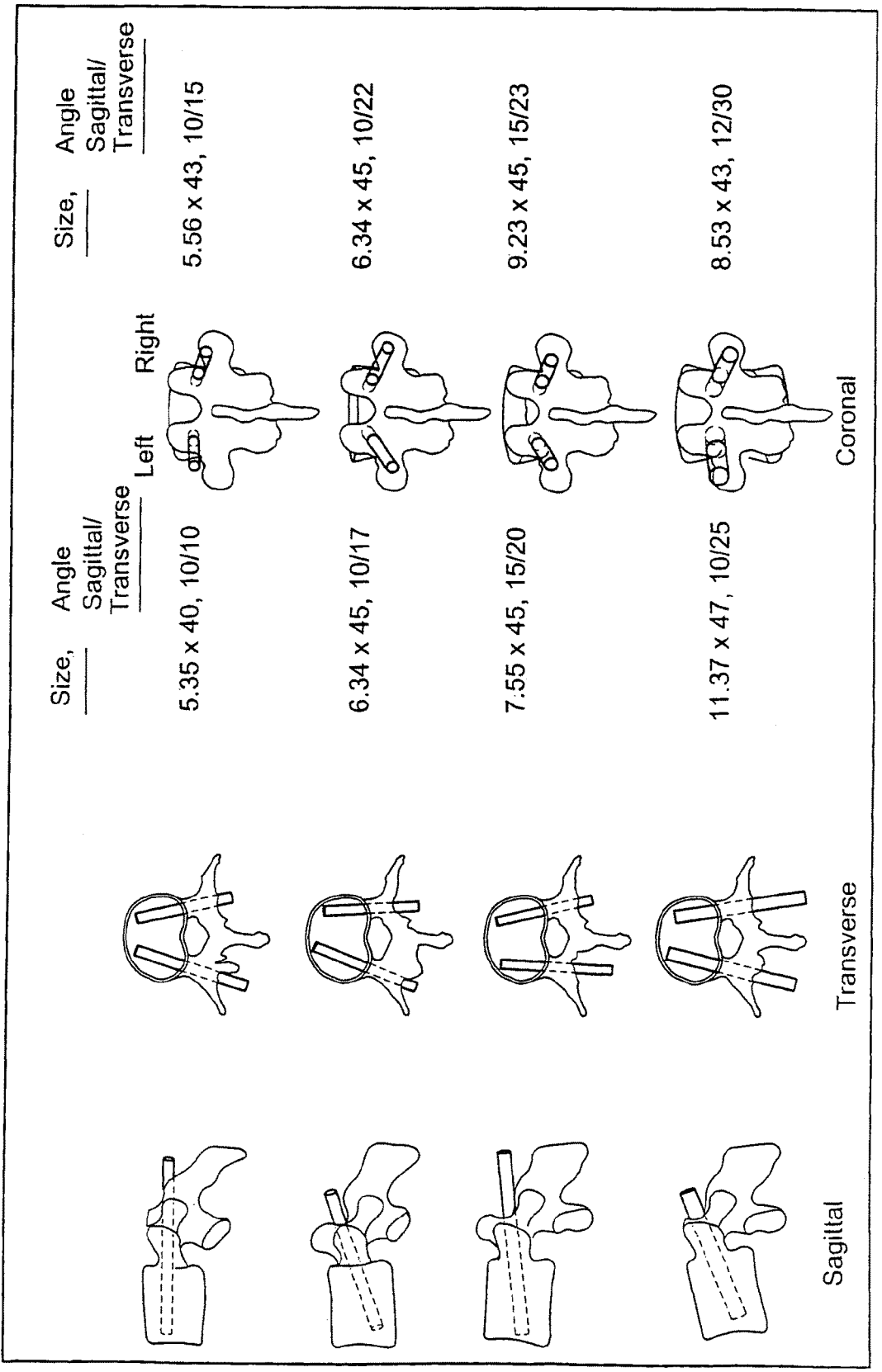
FIG. 13 is a computer generated schematic view of the screw placements as identified in the table of FIG. 12.

This tabulated data can then be utilized at this juncture for determination of the viability of using pedicle screws based on maximal pedicle screw diameter and length, as shown in FIG. 12, and also for placement of screws by a surgeon's preferred method. FIG. 12 also provides the individual pedicle base circumference outlines (coronal trajectory) from points A to B and their respective lengths. Actual screw sizes utilized will be based on surgeon selection of commercially available screws. A computer can automatically determine and generate this table once the surgeon provides the available screw size ranges in the selected pedicle screw system and concomitantly generate an idealized schematic AP (coronal), lateral and transaxial drawing with the data as shown in FIG. 13. Furthermore, this system provides surgeon override capabilities to choose a diameter different than the maximum available one on an individual vertebra basis and incorporates these override modifications into the summary data and diagrams.

Step 11—Manual Pedicle Screw Placement

The surgeon may then use the idealized schematic diagram and summary data for pedicle screw placement based on his or her preferred method.

Step 12a—Pedicle Base Circumference Outline Method—Manual Determination

Figure 4:
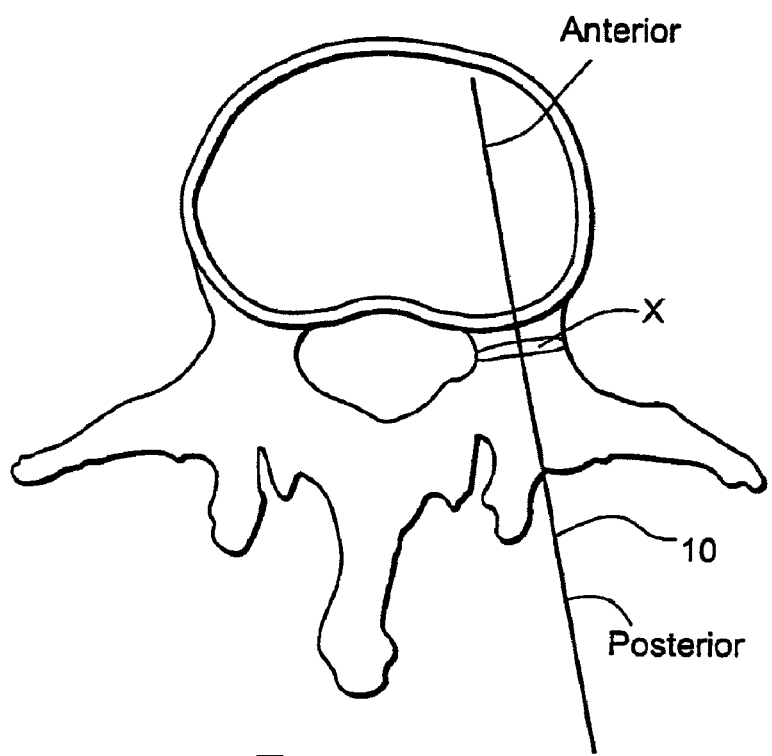
FIG. 4 is a computer image view of a hollowed out individual vertebra showing the generation of the straight line through the center of the isthmus and extending in opposite directions through the posterior pedicle cortex and toward the anterior inner cortex.
Figure 10D:
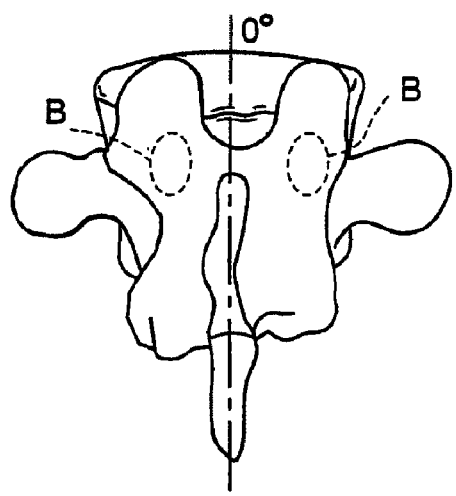
Figure 14A:
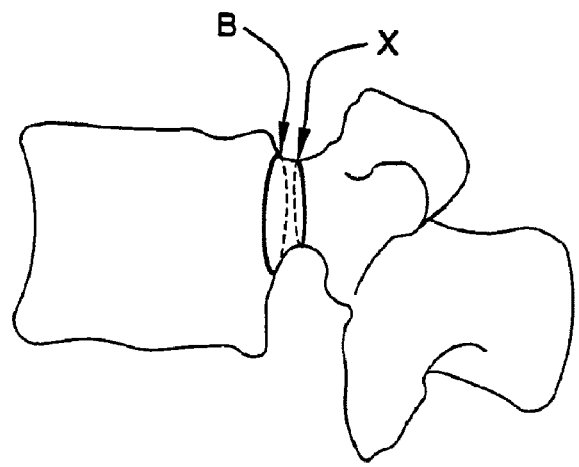
FIG. 14a is a schematic side elevational view of a vertebra showing the isthmus and the pedicle base circumference.

This method takes advantage of radiographic vertebral body anatomica landmarks to match the ideal pedicle screw trajectory in the coronal plane as shown in FIGS. 10d and 11. Specifically, the radiodensity circular lines seen on standard anteroposterior x-ray or fluoroscopic images correspond to the pedicle base circumferences. The pedicle base circumference B is defined as the cortical junction between the pedicle wall and its transition into the vertebral body. This pedical base circumference is distinctly different from the pedicle isthmus, but can in some instances be one and the same or super imposable for individual vertebra as seen in FIGS. 14a-4e.

Figure 14B:
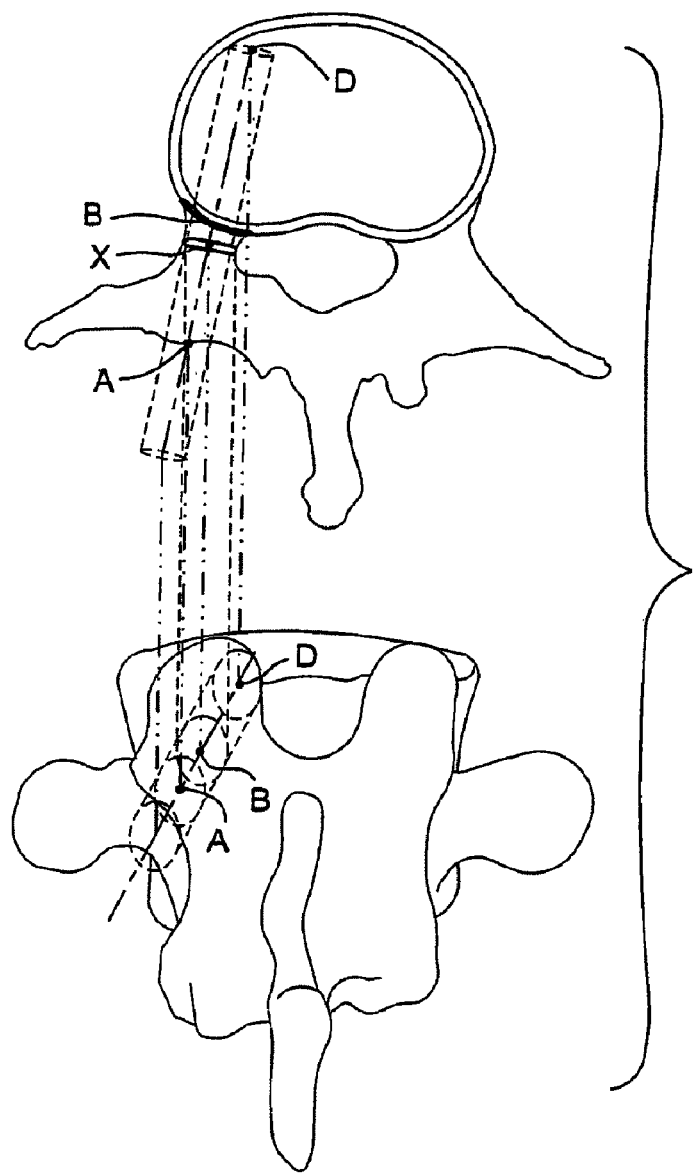
FIG. 14b is a schematic plan view of a vertebra showing the computer generated pedicle cylinder extending through the pedicle base circumference in the transverse and coronal planes.
Figure 14C:
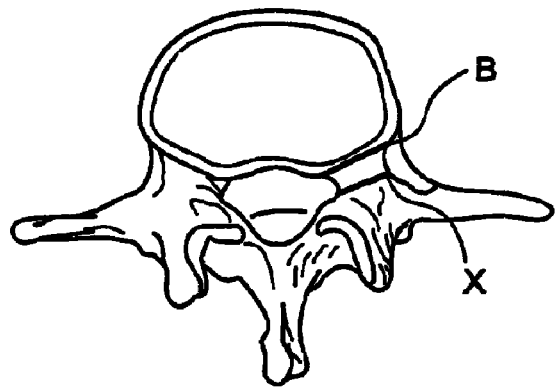
FIGS. 14c, 14d and 14e are plan views of vertebra in the lumbar, thoracic and cervical regions, respectively, showing the relationship between the isthmus and the pedicle base circumference in each vertebra.
Figure 14D:
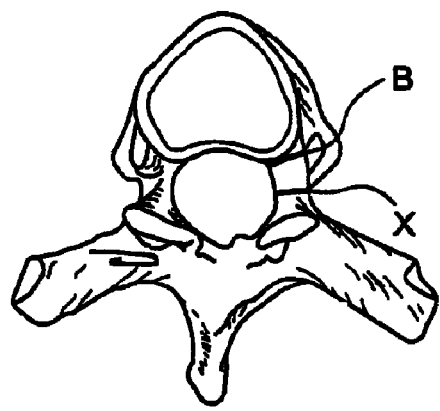
Figure 14E:
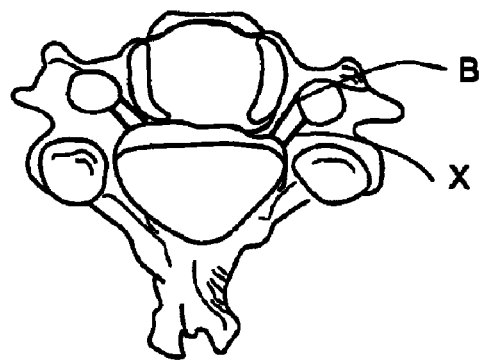
Figure 14F:
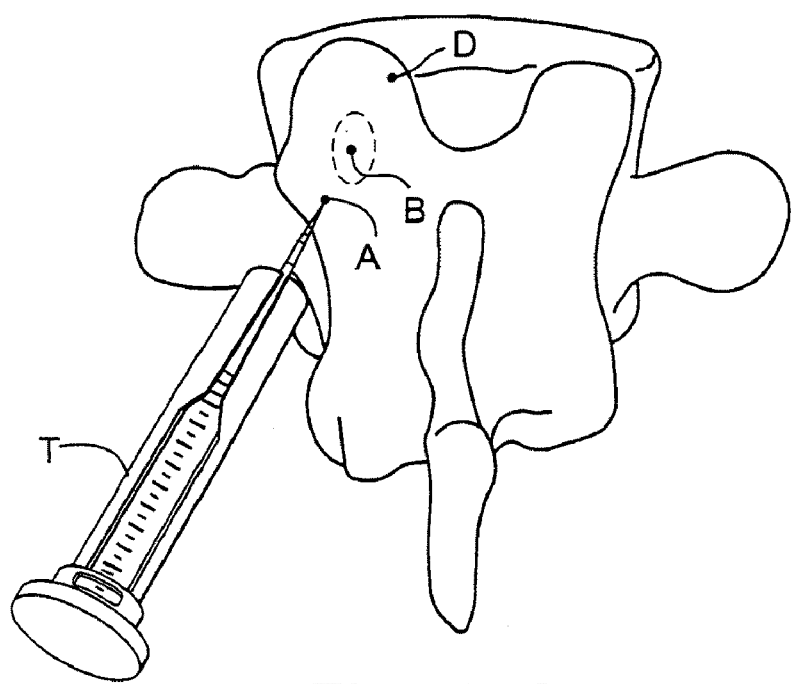
FIGS. 14f and 14g are schematic rear elevational views of a vertebra showing the positioning of an awl for creating the pedicle screw pilot hole in the vertebra.
Figure 14G:
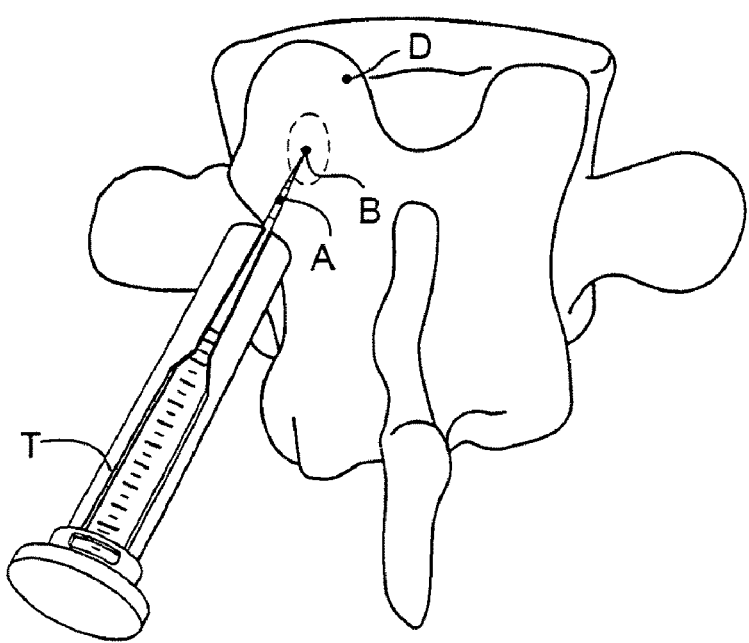
Figure 14H:
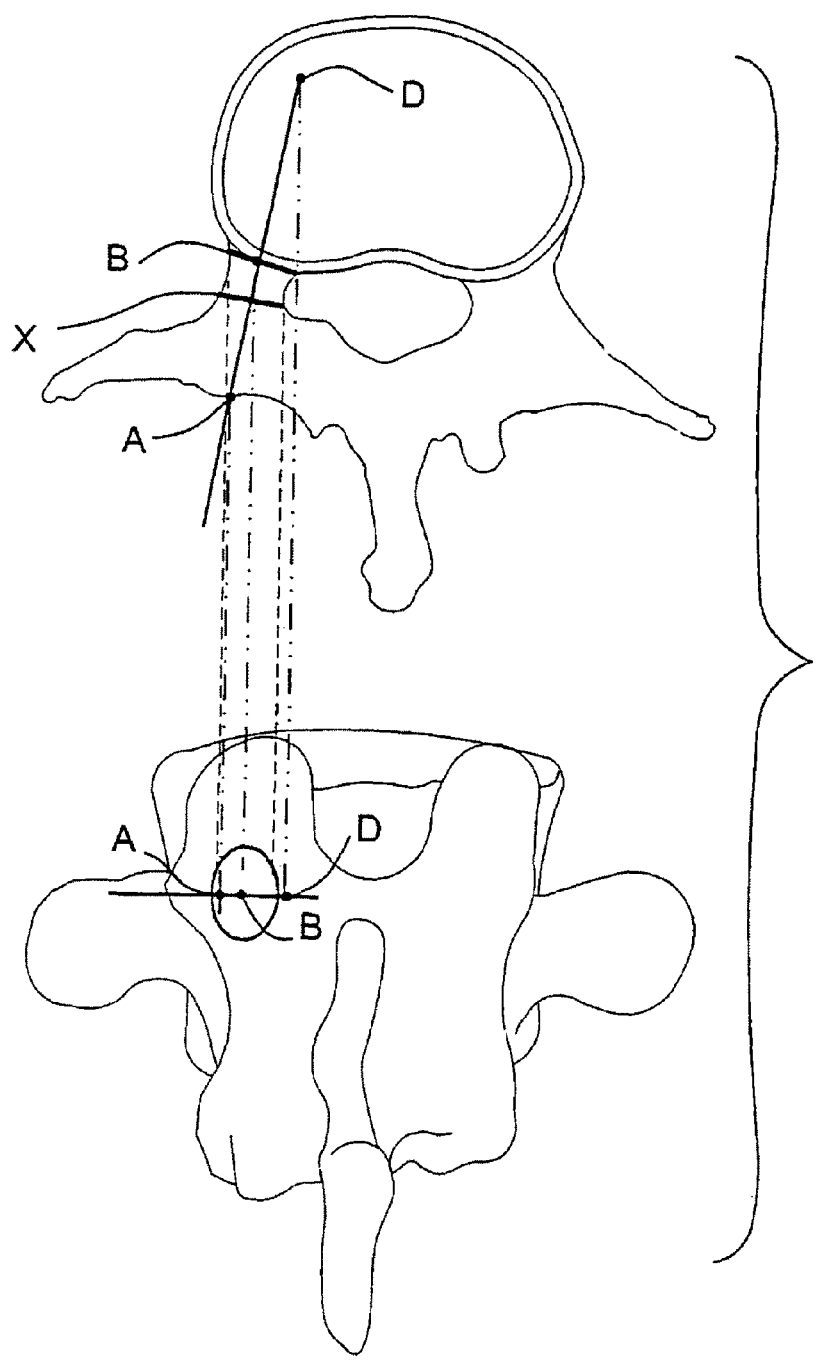
FIG. 14h shows schematic and aligned plan and rear elevational views of a vertebra with a manually determined pedicle screw directional line extending through the center of the pedicle base circumference.

For manual utilization of the pedicle base circumference technique, first the ideal trajectory through the pedicle isthmus X is manually determined using the corresponding transverse radiographic image through the pedicle as seen in FIG. 14b. The pedicle isthmus X is then measured to determine the maximum diameter pedicle screw. The trajectory is utilized for determination of the maximum pedicle screw length. The pedicle base circumference B is then determined by identifying the transition of the pedicle wall into the vertebral body as seen in FIG. 14b. Finally, the length A-B which corresponds to the starting point on the posterior cortex A up to the intersection with the pedicle base circumference B is measured and utilized for the calibration of a suitable tool such as variable length awl to be described hereinafter. Point A and point B should be centered with respect to the pedicle base circumference from the top (cephalad) and bottom (caudad) edges of the pedicle base circumference, as shown in FIG. 14h. The ideal trajectory and pedicle base circumference are then combined to determine where the point A lies with respect to the anteroposterior projection of the pedicle base circumference and where the point B lies within the pedicle base circumference. This pedicle base circumference outline will have a circular configuration to resemble the anteroposterior radiographic image for each individual vertebra.

For manual placement of pedicle screws, a standard fluoroscopy unit can be used to align the superior endplate of the respective vertebral body parallel to the fluoroscopic imaging. Furthermore, the vertebral body is centered when its superior end plate is fluoroscopically visualized by symmetric disc space with the cephalad vertebral body, and when the vertebral body is equidistant from each pedicle by having the pedicle base circumference outlines visually identical on the fluoroscopic AP image. This centering can still occur when there are other than two pedicles per vertebral body, such as congenital anomalies, tumors, fractures, etc. An appropriately calibrated variable length awl or other suitable tool T is then placed onto the posterior cortex of the corresponding vertebral body at pedicle pilot starting hold point A under fluoroscopic imaging and advanced into the pedicle up to point B as seen in FIGS. 14f and 14g. This placement is confirmed fluoroscopically and represents two points A and B on a straight line that co-aligns with the ideal trajectory. The tool T can be readjusted to lengthen and further advance into the vertebral body to point D or exchanged for another pedicle probing awl or similar tool The pedicle is then sounded for intraosseous integrity, the hold tapped and the appropriate diameter and length pedicle screw is placed transpedicularly into the vertebral body.

Figure 16:
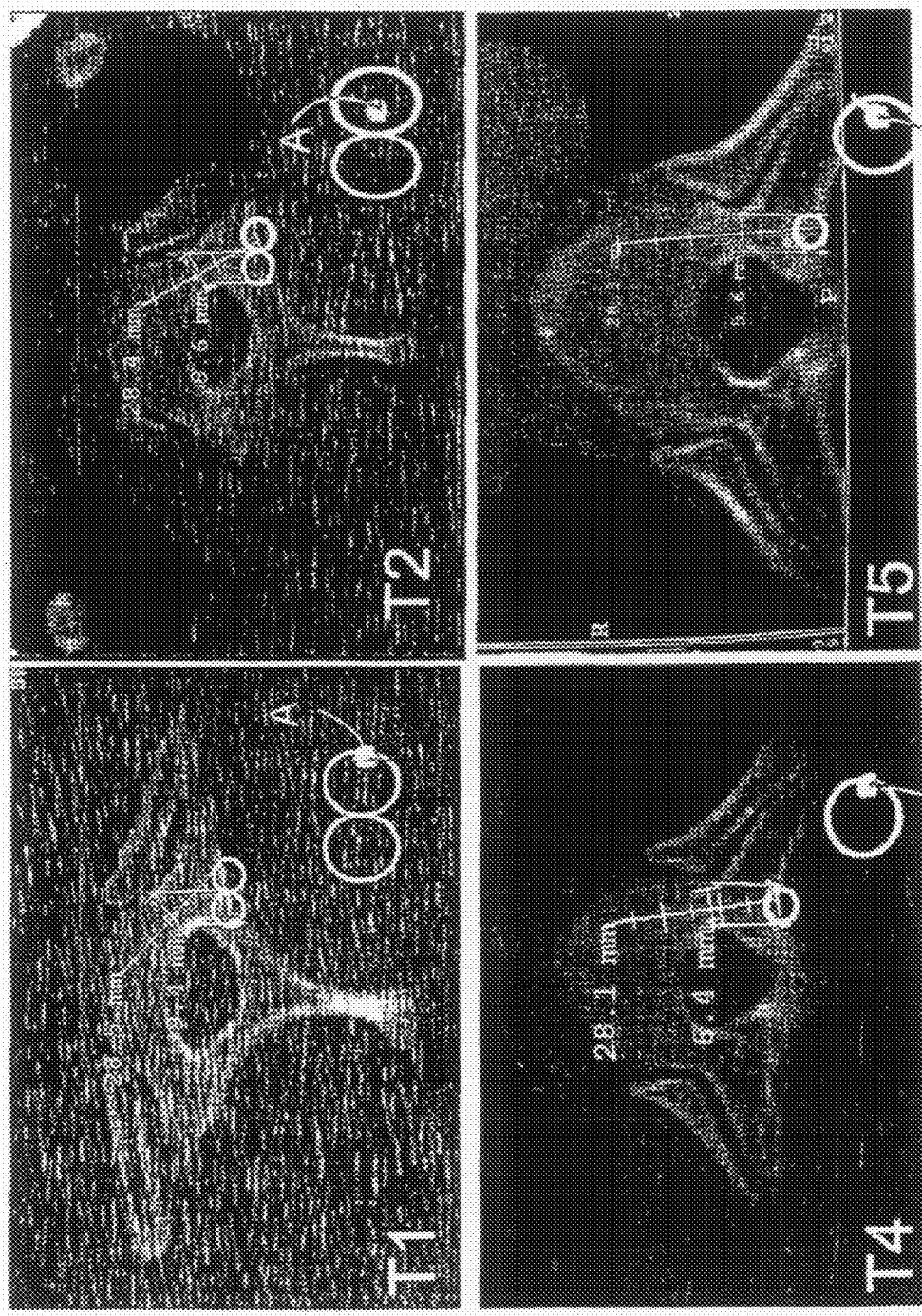
FIG. 16 shows CT transaxial views through the center of pedicles T1, T2, T4 and T5 demonstrating pedicle morphology, isthmus and determination of pedicle pilot hole entry points correlating with intraoperative AP fluoroscopic images of each respective vertebra.

In accordance with Step 12a, CT transaxial views through center of pedicles T1, T2, T4, T5, as shown in FIG. 16, demonstrate pedicle morphology, isthmus and manual determination of pedicle pilot hold entry points correlating with intraoperative AP fluoroscopic images of each respective vertebra. Pedicle screw length, diameter and trajectory have already been determined. The pedicle base circumference outline is represented as the circle on the bottom right hand corner and is utilized as a consistent intraoperative marker for identifying pedicle pilot hold starting points. For example, the starting points A for both T1 and T2 pedicles are approximately 2 pedicle base circumferences and 1.25 pedicle base circumferences, respectively, as seen on the AP fluoroscopic pedicle base circumference seen intraoperatively (indicated by the dot within the circle), The T4 and T5 pedicle pilot holes are 0.9 and 0.8 pedicle base circumferences, respectively.

Step 12b—Pedicle Base Circumference Outline Method— Semi-Automated

This method is similar to Step 12a except that points A and B and pedicle base circumference outline is determined by a computer after building the computer generated pedicle cylinders concentrically. This data is then summarized as in FIG. 12. This data also includes the sagittal and transverse trajectory angles measured in degrees with respect to the superior endplate and midline vertebral body. A variable length awl or other tool, for example. may then be appropriately adjusted to specific pedicle length A-B summarized in FIG. 12 and screws placed with standard fluoroscopy as described in Step 12a.

Step 12c—Pedicle Base Circumference Outline Method— Fully Automated

Figures 15A, 15B:
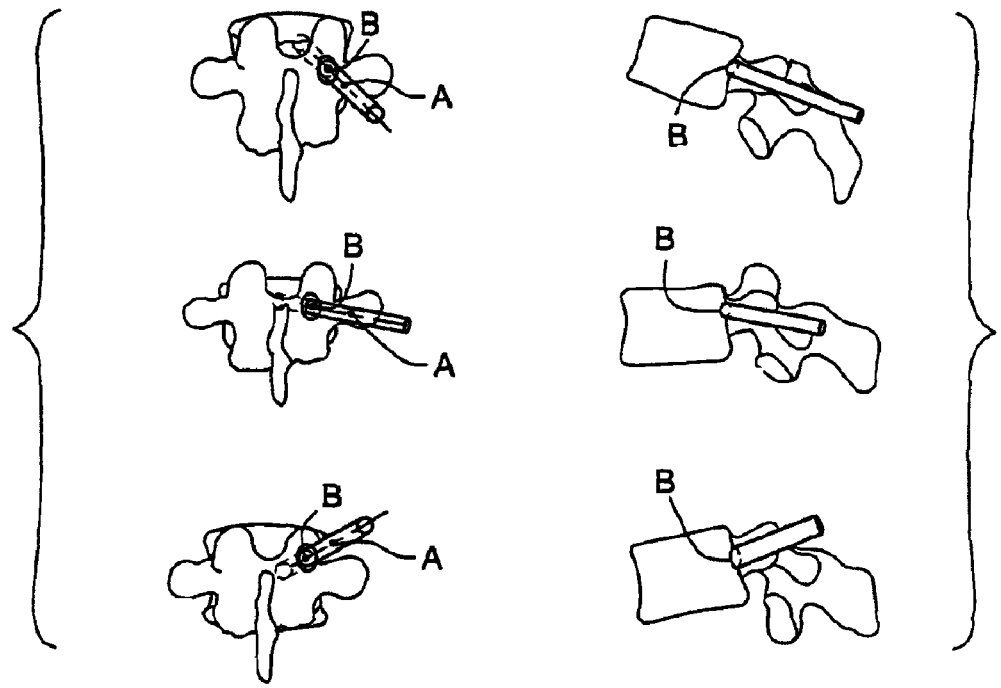
FIGS. 15a, 15c and 15e show schematic rear elevational views of a vertebra in different orientations with a computer generated pedicle screw cylinder extending through the pedicle base circumference thereof.
FIGS. 15b, 15d and 15f show schematic side elevational views of the vertebra illustrated in FIGS. 15a, 15c and 15e, respectively.
Figures 15C, 15D:
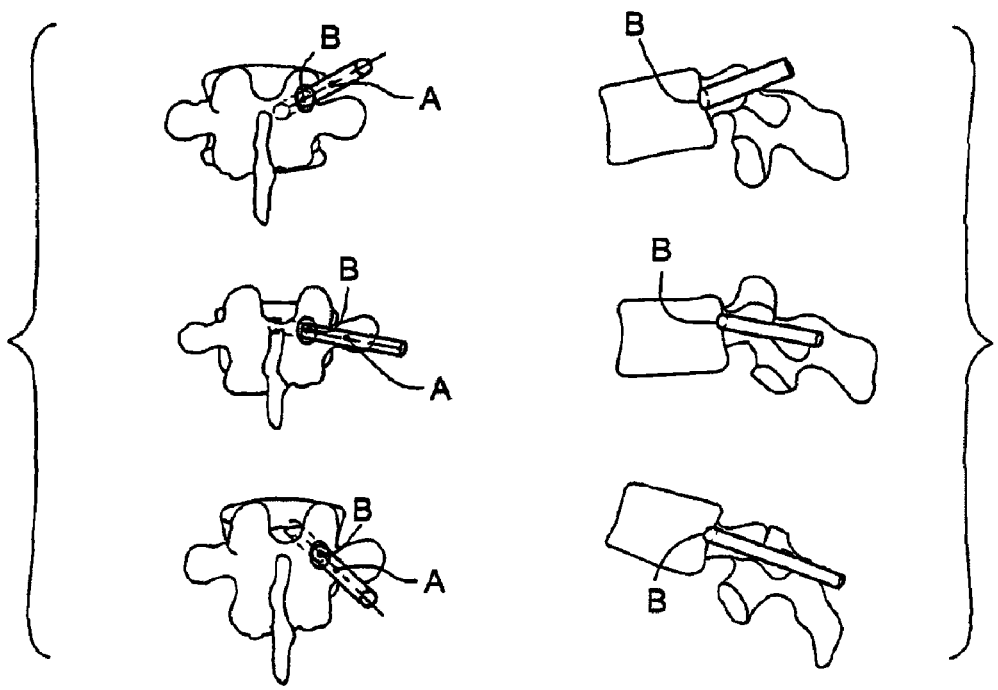
Figures 15E, 15F:
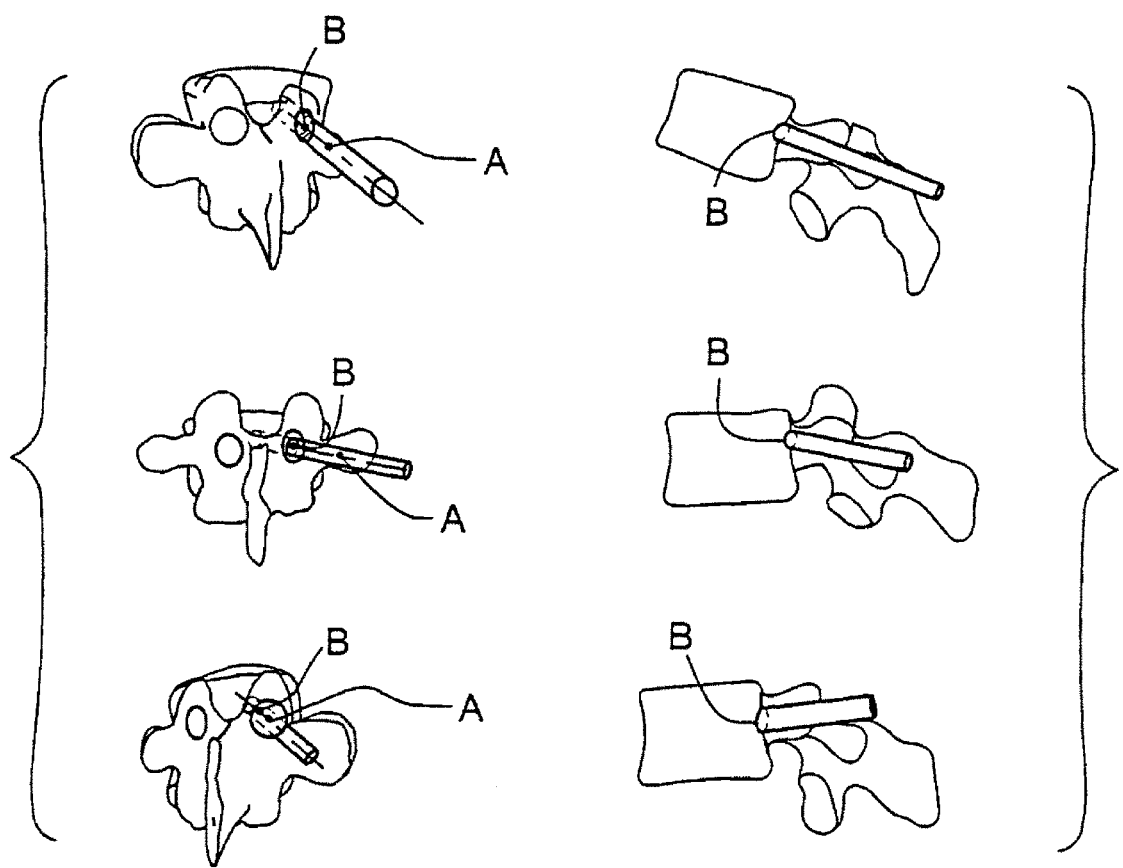

This method further expands the present technique to allow for real-time imaging and multiple vertebral body visualization for pedicle screw placement. The data generated is the same as in FIG. 12 except that the pedicle base circumference outlines and identified points A and B are dynamic and do not require the vertebral body to be centered or have the superior end plate parallel to the fluoroscopic imaging as in Steps 12a and 12b. The fluoroscopically imaged vertebral bodies are registered by any suitable method to the computer generated vertebral bodies with their corresponding computer generated pedicle cylinders. The points A and B are then visualized as seen in FIGS. 15a ... 15c and 15e and displayed as in FIG. 12 as updated real-time imaging. A variable length awl or other tool. for example. may then be adjusted to appropriate length for starting at point A and advancing to point B for each respective vertebra. It is noted that any suitable tool, such as a nonadjustable awl, may be used other than an adjustable awl in accordance with the methods of the present invention.

Step 13—Adjustable Variable Length Awl

The distance from point A to point B (FIG. 14b), posterior cortex to intersection with pedicle base circumference, is utilized to set the length A-B on an adjustable variable length awl constructed in accordance with the present invention. This awl is used to establish the pedicle pilot hole under fluoroscopic imaging. The pedicle pilot hole forms the first step in a series of steps for actual placement of a pedicle screw. The pilot pedicle hole is started at the identified starting point A indicated by the computer generated pedicle cylinders and advanced to point B once it is fully seated.

Figure 17A:
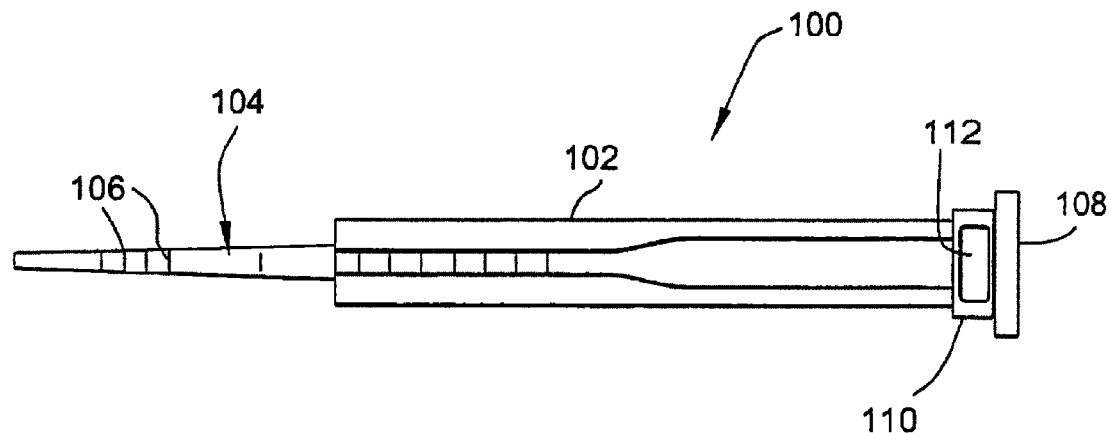
FIGS. 17a and 17b are side elevational views of different embodiments of an adjustable awl of the present invention.

Referring to FIG. 17a, the awl 100 comprises a cannulated radiolucent housing 102 with an open end which movably supports a radio opaque awl member 104. The awl 100 is fully adjustable for variable lengths to correspond to length A-B and also configured to prevent advancement of the awl further than any distance A-B as seen in FIG. 14b and other drawing figures.

A surgeon can adjust the awl to any length from point A to point D, the final screw length, in FIG. 14b once the distance A-B has been radiographically confirmed. The awl 100 preferably is of such construction to tolerate being struck with a mallet or the like and is of a diameter narrow enough to be used percutaneously. To facilitate visualization of depth, the awl member 104 may be marked in color or otherwise at fixed increments 106, such as 5 mm or 10 mm.

The awl 100 may be provided with a solid head 108 at its outer end for striking, and with any suitable locking mechanism 110, such as a locking screw mechanism, for locking the awl member 104 in a desired position relative to the housing 102. The awl may also be provided with a window 112 or other indicia for indicating the position or length of the awl member 104. FIGS. 14f and 14g show an awl being advanced into the pedicle to create the screw pilot hole.

Figure 17B:
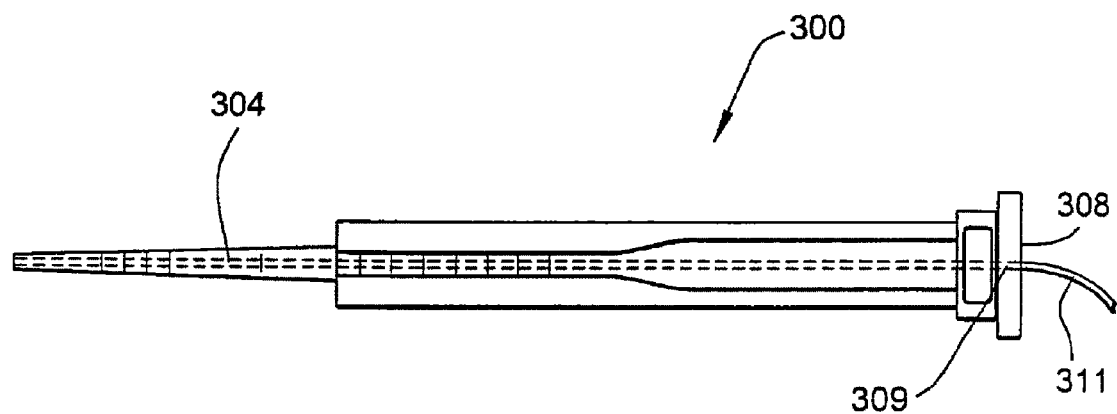

FIG. 17b illustrates a modified adjustable awl 300 which comprises a cannulated or hollow awl member 304 and a head 308 with a central aperture 309 such that a guide wire 311 may extend through the head and through the awl member 304 to its inner end. After the pilot hole is formed by the awl 300. the guide wire 31.1 max be left in position in the pilot hole to facilitate its location during subsequent steps leading to the installation of the pedicle screw.

Step 14 Dual Ring Co-Aligned Technique

For automated intraoperative pedicle screw placement the dimensionally true three dimensional spine model with computer automated placed pedicle screw cylinders defining length, diameter and trajectory is utilized. In addition, the pedicle base circumference outline data is utilized to facilitate registration with intraoperative imaging.

Figure 18A:
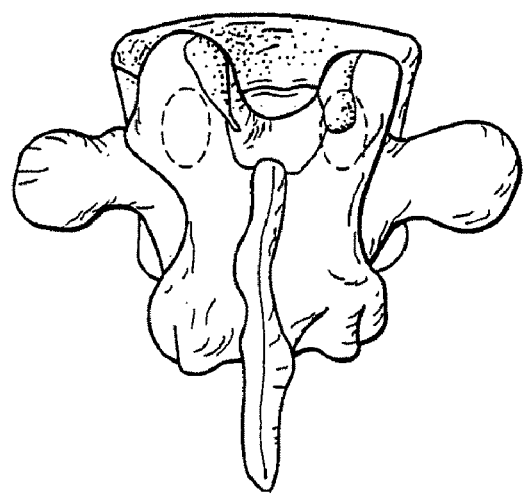
FIG. 18a is a schematic view of an intraoperative AP fluoroscopic image of individual vertebral and pedicle base circumferences.
Figure 18B:
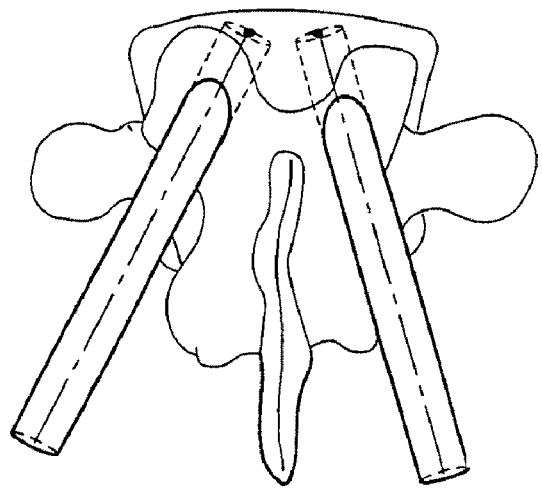
FIG. 18b is a schematic view of computer generated three dimensional images of vertebra with computer placed pedicle cylinders and pedicle base circumferences.
Figure 18C:
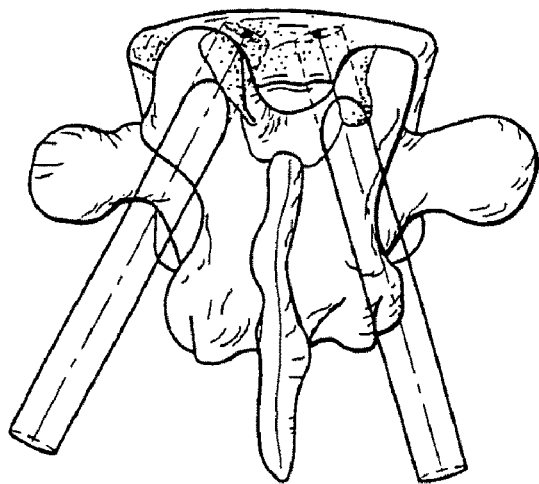
FIG. 18c is a schematic view of the registered images of FIGS. 18a and 18b.

Real-time intraoperative fluoroscopy is utilized for accurate registration with the three dimensional model on an individual vertebral basis. This fluoroscopic vertebral body image is centered on the monitor and identified by the surgeon for its specific vertebral body identifier (i.e., T2, T3, etc.). The corresponding dimensionally true three dimensional individual vertebral model is registered to this fluoroscopic image as shown schematically in FIGS. 18a, 18b and 18c. This can be performed on either surgically exposed spines or percutaneously.

The registration occurs by utilizing internal vertebral body bony landmarks. These landmarks are the pedicle base circumferences seen on the fluoroscopic image which arise from the confluence of the pedicle cortical walls joining the vertebral body. As hereinbefore explained, these pedicle base circumferences form either circular or elliptical shapes which can change configuration and square area based on vertebral body rotation with respect to fluoroscopic imaging.

The intraoperative fluoroscopic and computer spine generated pedicle base circumference outlines are then registered. Precision of registration is obtained by assuring outlines are superimposed and measured square areas are equal and by assuring distance between pedicles is equal. This method of registration eliminates the requirement of having a radiographic marker anchored to the patient's skeleton, which is particularly disadvantageous, for percutaneous applications. This method also allows for free independent movement of one vertebral body to another demonstrating compliance of this computer generated model, which is particularly useful in spines with instability. The surgeon confirms adequacy of registration of pedicle base circumferences intraoperatively in order to proceed with screw placement.

This method allows for magnification or reduction of the computer generated model to match the intraoperative fluoroscopic image.

Figure 19A:
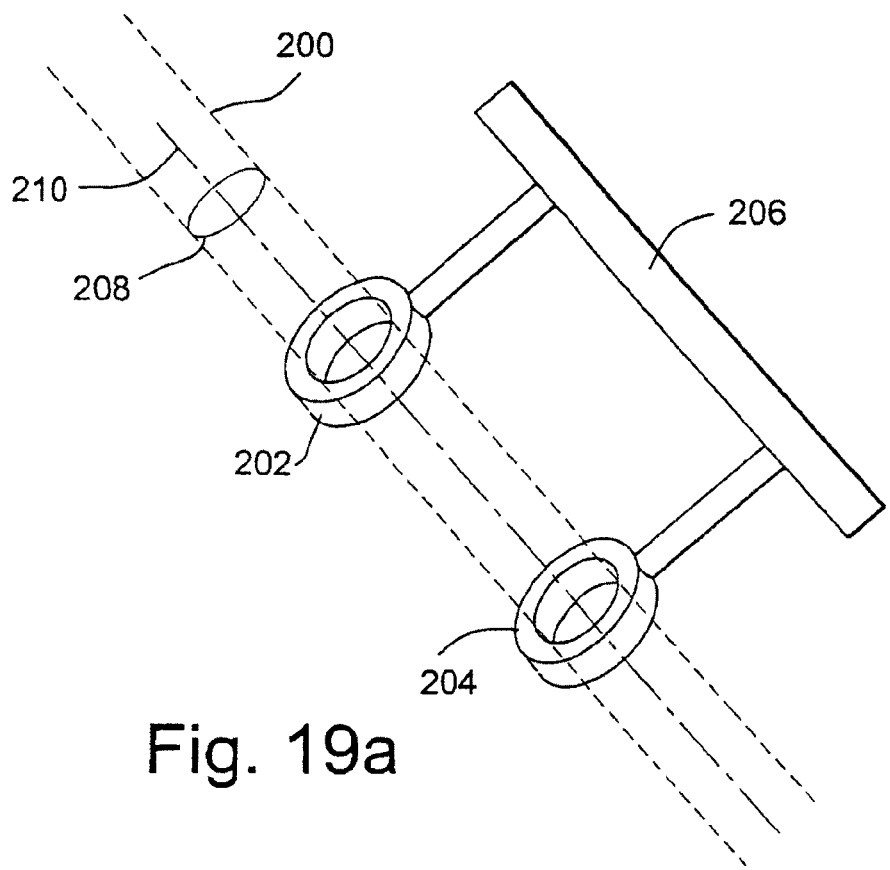
FIG. 19a is a schematic side elevational view of a dual ring pedicle screw aligning apparatus constructed in accordance with the present invention.
Figure 19B:
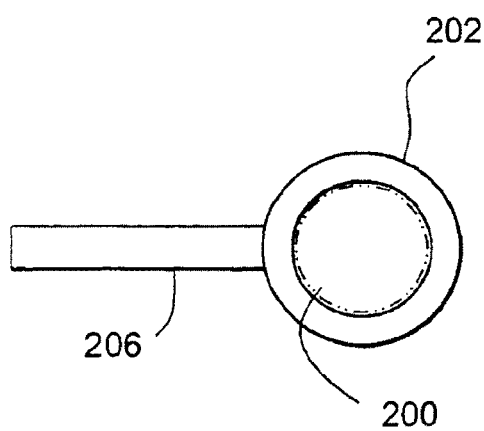

The full three dimensional image which now includes the computer generated pedicle base circumference and pedicle cylinder is then projected superimposed on the intraoperative fluoroscopic image. As shown in FIGS. 19a and 19b. the computer pedicle screw cylinder 200 is then projected out of the patient's body through the posterior cortex and is intercepted by and extends through two separate and collinear rings 202, 204. The rings are mounted on a suitable support frame 206 anchored to the patient's bed or other support (not shown) and are sized to allow interception of the computer cylinder image and to allow placement of drilling cannulas. The first ring 202 intercepts the computer pedicle screw cylinder near the posterior cortical region 208 or just outside the body and the second ring 204 intercepts the computer pedicle screw cylinder at any desired distance from the first ring 202. The longer the distance between the two rings the greater the accuracy of screw placement. The interception of the computer pedicle cylinder by the rings 202, 204 is displayed on a computer monitor which demonstrates movement of the rings with respect to the computer pedicle cylinder 200.

Figure 19C:
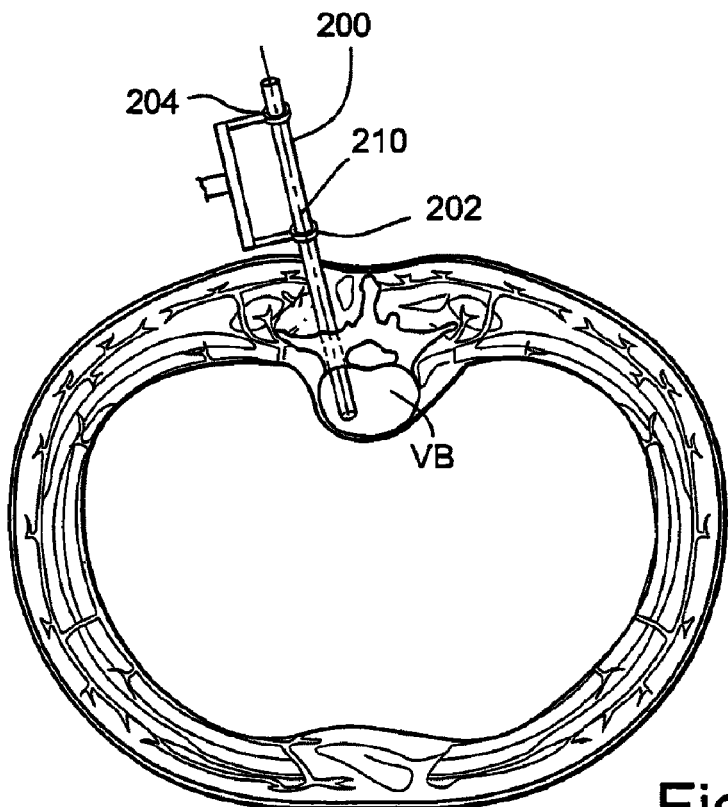
FIGS. 19c and 19d are schematic plan views of a vertebra showing the use of the dual ring pedicle screw aligning apparatus in a percutaneous environment and an open surgical environment, respectively.
Figure 19D:
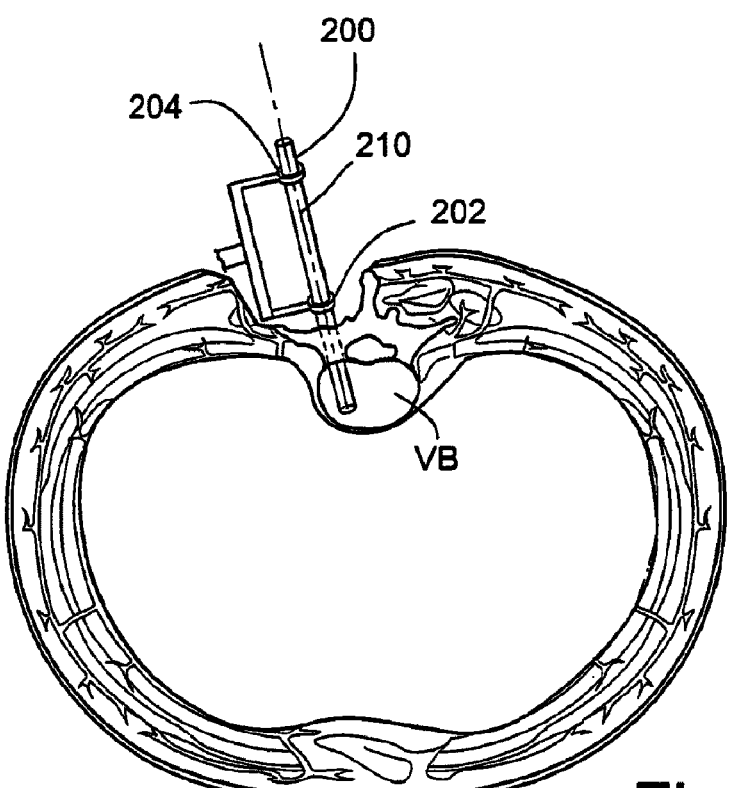

FIGS. 19c and 19d illustrate the computer generated cylinder 200 and line 210 projecting out from a vertebral body VB through the rings 202, 204 in a surgically open environment and a percutaneous environment, respectively.

Figure 20:
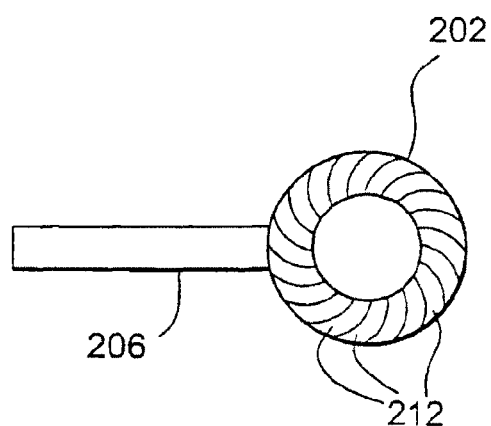
FIG. 20 is a front elevational view of a modified dual ring pedicle screw aligning apparatus.

Interception of the pedicle cylinders occurs on two levels. The computer pedicle cylinders 200 are comprised of a central line 210 with surrounding cylinder. First, the rings 202, 204 need to be centered to both the central line 210 and pedicle cylinder 200. Second, the rings are registered to the vertebral body so their movements can be followed on the computer monitor such as through LED devices. Third, the rings are constructed to have inner diameters to allow matching of diameters corresponding to the diameter of the computer generated pedicle cylinders 200. A variety of removable rings with different diameters may be provided to allow utilization of any pedicle screw system desired by the surgeon. Fourth, the rings can be constructed to be adjustable in any suitable manner to allow for variable diameters to allow matching of diameters corresponding to the diameter of the computer generated pedicle cylinder as shown in FIG. 20 where the ring 202 is formed of movably connected sections 212 that can be rotated to vary the ring diameter. Registration of the rings with the computer pedicle cylinder is identified and confirmed on the computer monitor.

The two co-aligned ring 202, 204 now form the conduit in which to place a drilling cannula 214 (FIGS. 21a and 21b) which is also secured to the frame 206 anchored to the patient's bed or other support. Inside this drilling cannula 214 is placed a solid cannula member 216 (FIGS. 21a and 21b), or a specialized inner cannula member 218 (FIGS. 2a and 22b) may be used which has multiple narrow movable and longitudinal metal parallel pins 220 therein and is open centrally to allow for drill placement. The multiple pins 20 allow for the inner cannula member 218 to rest evenly on an uneven surface. This feature provides additional stability at the posterior cortex drilling area to avoid toggling of the drill bit.

Additionally, the specialized inner cannula member 218 allows for retraction of the multiple parallel pins to allow fluoroscopic visualization of drilling within the pedicle. Either method may be used by the surgeon.

The pedicle is then drilled to its desired precalibrated depth and not exceeding the predetermined pedicle screw length. The pedicle is then sounded with a pedicle probe to assure osseous integrity.

For actual screw placement. a specialized slotted outer cannula 230 (FIGS. 23a and 23b) is placed collinear and onto the co-aligned two rings 202, 204 which are removably mounted on the support frame. This specialized cannula 230 is also secured to the support frame or other anchoring device. The rings are then removed by rotating them approximately ninety degrees (not shown) and withdrawing them from the cannula 230. The slotted cannula's adjustable inner diameter is sufficient to accommodate any pedicle screw diameter threaded and variable head size. The appropriate pedicle screw (not shown) is placed into its holding screwdriver, placed into the slotted cannula and then placed into its respective pedicle.

Figure 23A:
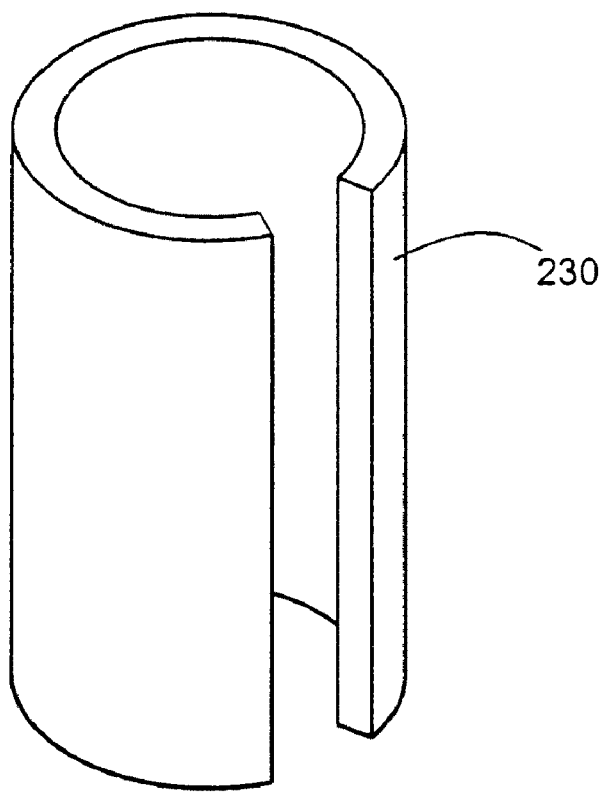
FIG. 23a is a perspective view of a slotted outer cannula for use with the dual ring aligning apparatus of FIGS. 19a and 19b.
Figure 23B:
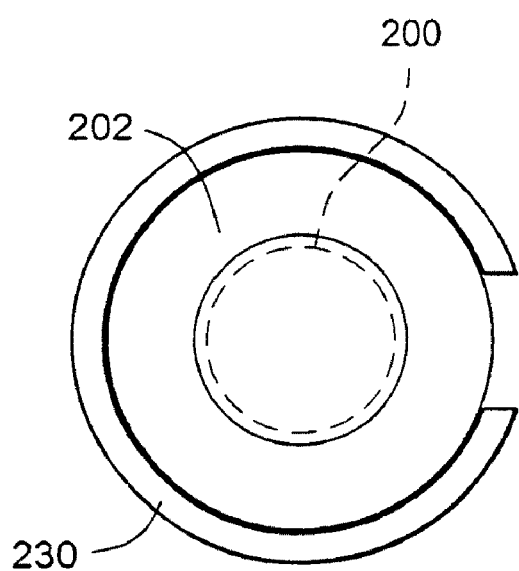
FIG. 23b is a front elevational view of the slotted cannula shown in FIG. 23a with an aligning ring disposed therein.

For the modified adjustable coaligned rings shown in FIG. 20, the slotted cannula 230 in FIG. 23a can be used or alternatively, the rings 202, 204 may be left in position and adjusted to a fully open position to accommodate a screwdriver placed into and through the rings.

Step 15

There are currently commercially available software packages capable of producing intraoperative registration of intraoperative fluoroscopy images with preoperative three dimensional images of a patient's spine. Such capabilities can be integrated with the methods of the present invention to provide summary numerical data and idealized illustrated diagrams. The latter information will provide the basis for actual screw placement as described herein or by a surgeon's preferred choice.

Step 16

Figure 24:
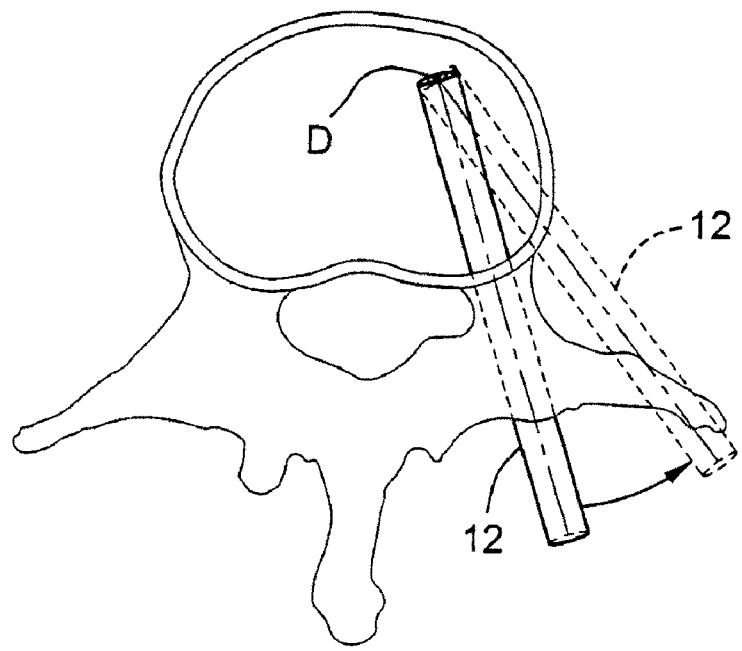
FIG. 24 is a schematic view of a hollowed out vertebra showing different pedicle screw trajectories in a centered or ideal trajectory and an extraosseous or extrapedicular trajectory that is offset tangentially from the centered trajectory.

For surgeons who prefer to place screws extraosseous or extrapedicular because the pedicle screw sizes are too small to accommodate available screw sizes, planned eccentric screw placement in large pedicles or planned straight ahead versus anatomic axis screw placement. the present invention allows this canability. It accomplishes this by obtaining all idealized data and then allows a surgeon to offset the pedicle pilot hole entry placement at any desired distance tangentially from the ideal trajectory. i.e. the anterior screw position is the pivot point D from which a computer pedicle cylinder 12 is generated, as shown in FIG. 24.

Furthermore, these changes will be automatically recorded to generate new idealized AP, lateral and transaxial schematic diagrams incorporating these changes. This data can be used for placement of screws by either the pedicle base circumference method, an automated aligning method or a commercially available CT/fluoroscopy registration method. For the pedicle base circumference method, new pilot hole lengths are determined to allow for proper length of an awl or other tool.

Figure 25:
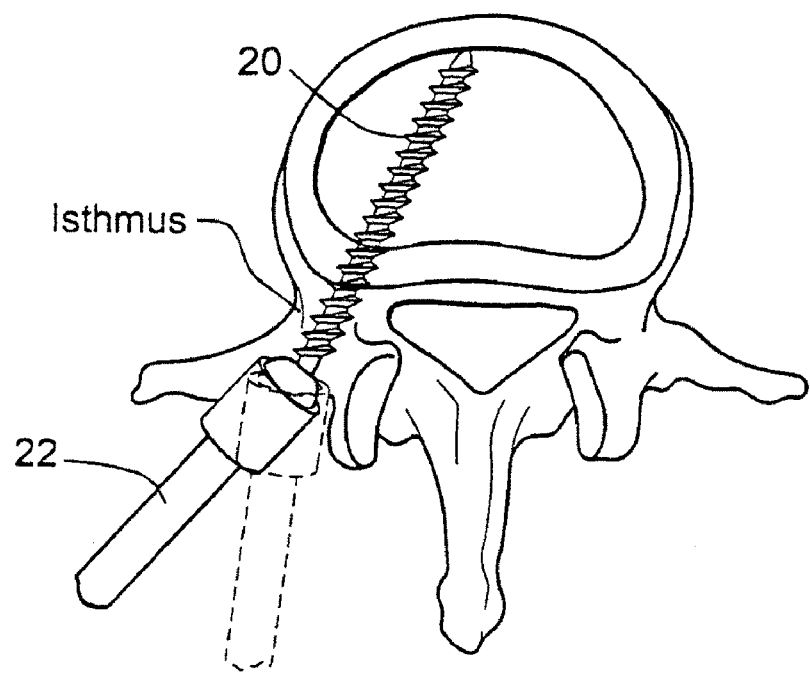
FIG. 25 is a schematic plan view of a vertebra showing the installation of a pedicle screw in accordance with the method of the present invention.

As an illustrative embodiment, FIG. 25 shows schematically the installation of a pedicle screw 20 by a screwdriver 22 or the like through the center of the isthmus X in accordance with the present invention.

Step 17

Figure 26A:
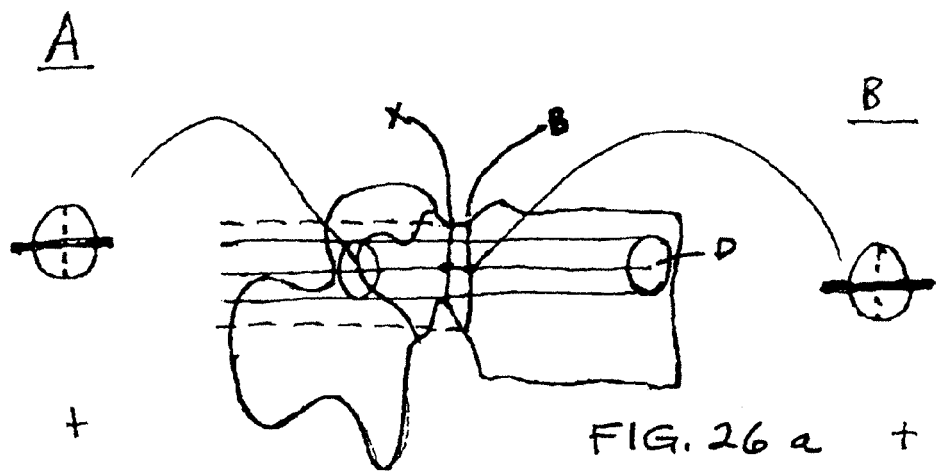
FIGS. 26a, 26b and 26c are schematic side elevational, plan and rear elevational views, respectively, of a vertebra showing the computer-generated pedicle cylinder extending through the pedicle base circumference and isthmus.
Figure 26B:
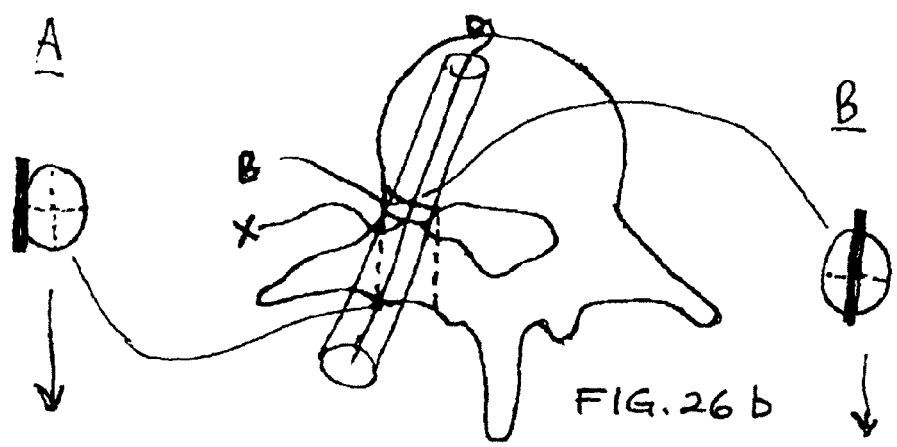
Figure 26C:
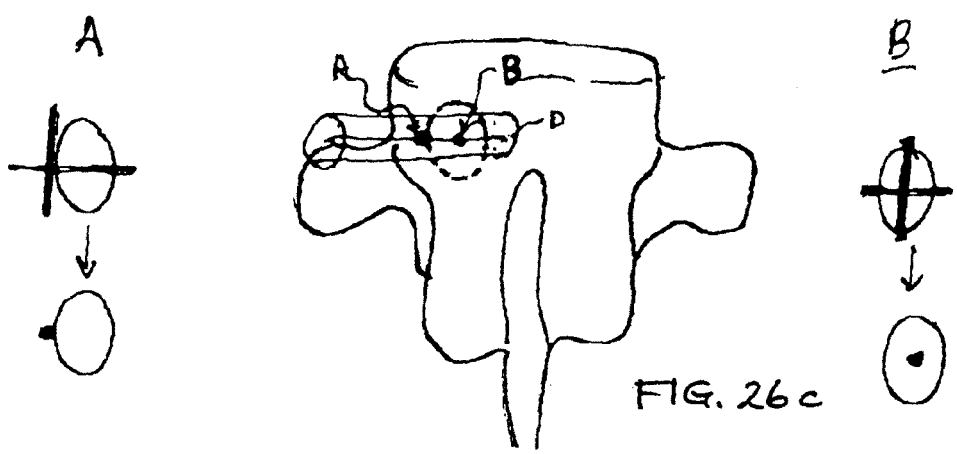
Figure 27A:
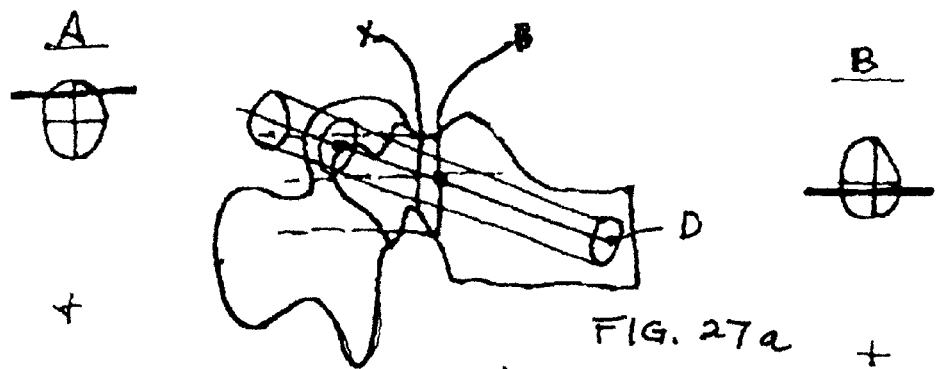
FIGS. 27a, 27b and 27c are schematic views similar to FIGS. 26a, 26b and 26c, respectively, showing the computer generated pedicle cylinder for eccentric placement in vertebras which have fractures and associated abnormal anatomy.
Figure 27B:
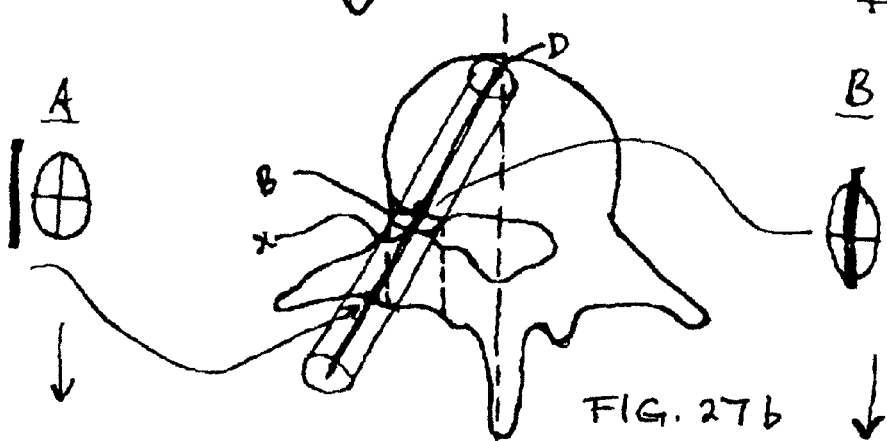
Figure 27C:
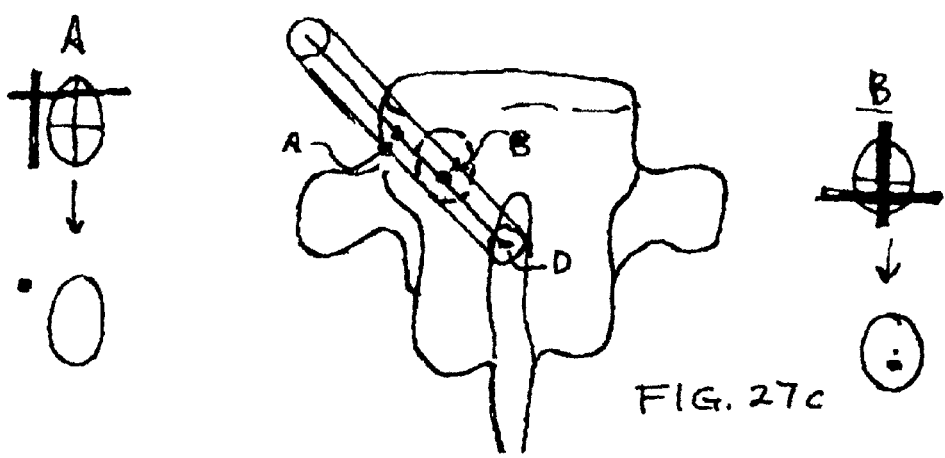
Figures 28A, 28B, 28C:
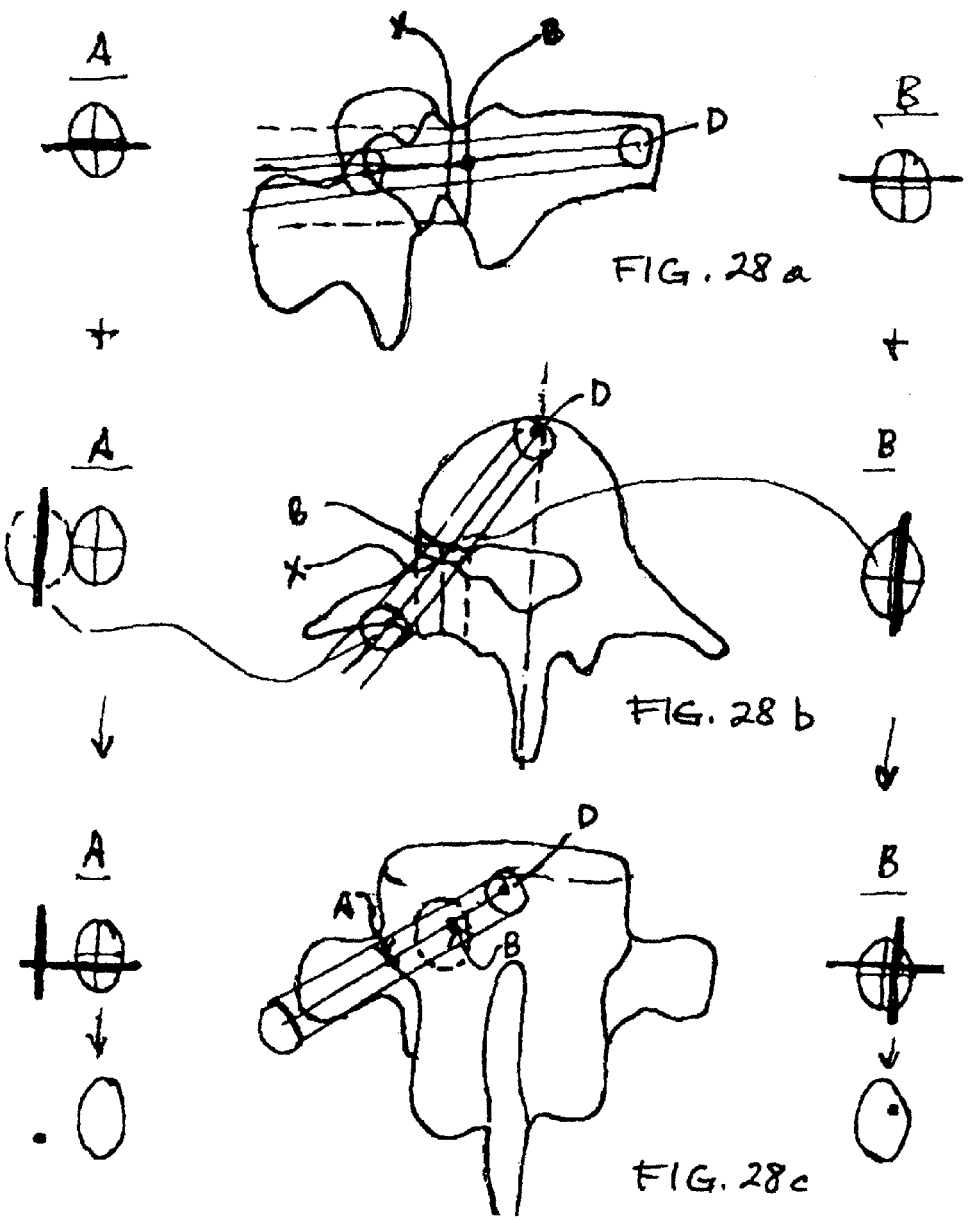
FIGS. 28a, 28b and 28c are schematic views similar to FIGS. 27a, 27b and 27c, respectively, showing the computer generated pedicle cylinder for a modified eccentric placement in vertebras.

The new procedure is an extension of the methods described herein for pedicle cylinder building using the pedicle isthmus as the fulcrum for straight line development. The major difference is that this new procedure modifies the approach described herein by purposely proceeding with planned eccentric placement for those vertebras which have pathologic or traumatic features and associated vertebral body abnormal anatomy. For normal vertebral body without endplate fractures or compression the herein described concentric trajectory through the pedicle is chosen for pedicle cylinder building as seen in FIGS. 26a, 26b and 26c.

Step 18

For eccentric pedicle cylinder building the fulcrum for straight line development remains the narrowest portion of the vertebral body, the pedicle isthmus X. However, once the isthmus is determined, the next step is determination of Point D within the vertebral body. This point D is equidistant from the superior and inferior endplates and in the center of the vertebral body abutting the anterior inner cortical wall. A computer then draws a line from Point D to the center of the pedicle isthmus exiting out the posterior pedicle cortex. FIGS. 27a-c and 28a-c demonstrate trajectory determination for vertebral bodies which have sustained superior endplate and inferior endplate compression fractures, respectively. The FIGS. 25a-c, 27a-c and 28a-c show the planes in the sagittal and transverse where starting points A and B can reside. The coronal image demonstrates the effect of combining both the sagittal and transverse planes to correctly identify the starting points A and B as seen in FIG. 12.

Step 19

A computer then builds this cylinder concentrically in a radial direction until it comes into contact with the highlighted cortex. A computer then determines the ideal pedicle trajectory, diameter and length and records this into a table (FIG. 12). The pedicle base circumferences identify the Points A and B for accurate placement of the combined radioopaque/radiolucent and color banded awl/guide wire into the pedicle. It is advanced to the appropriate depth distance A-B recorded in FIG. 12.

Step 20

Figure 29:
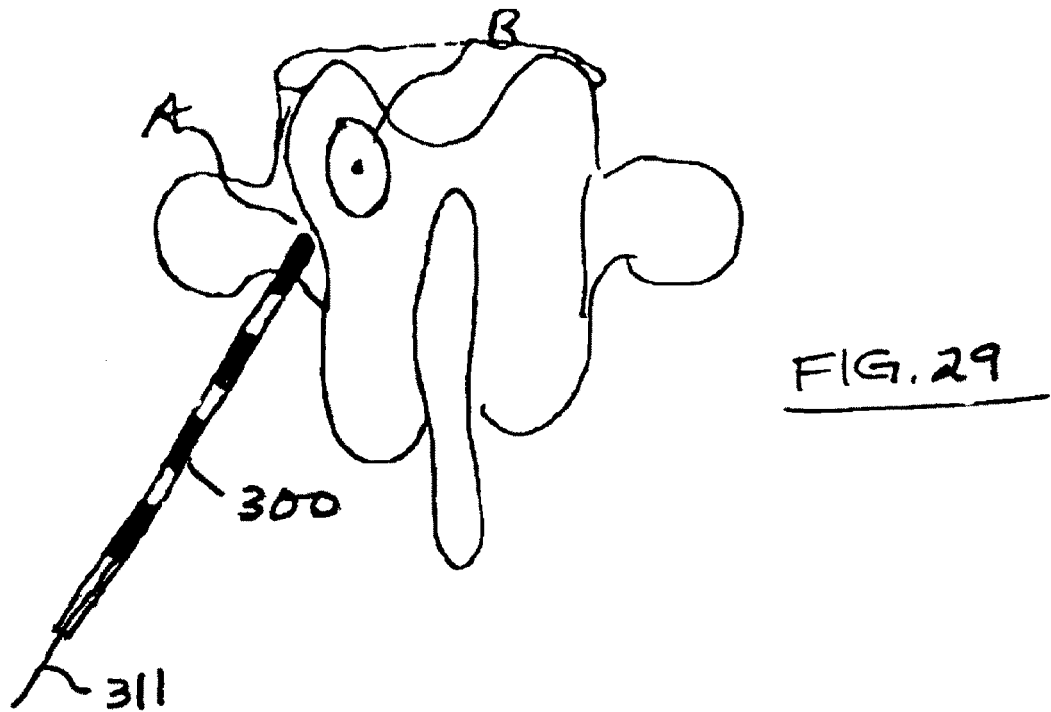
FIG. 29 is a schematic rear elevational-view of a vertebra and an awl/guide wire to be inserted therein in accordance with the method of the present invention.
Figure 30:
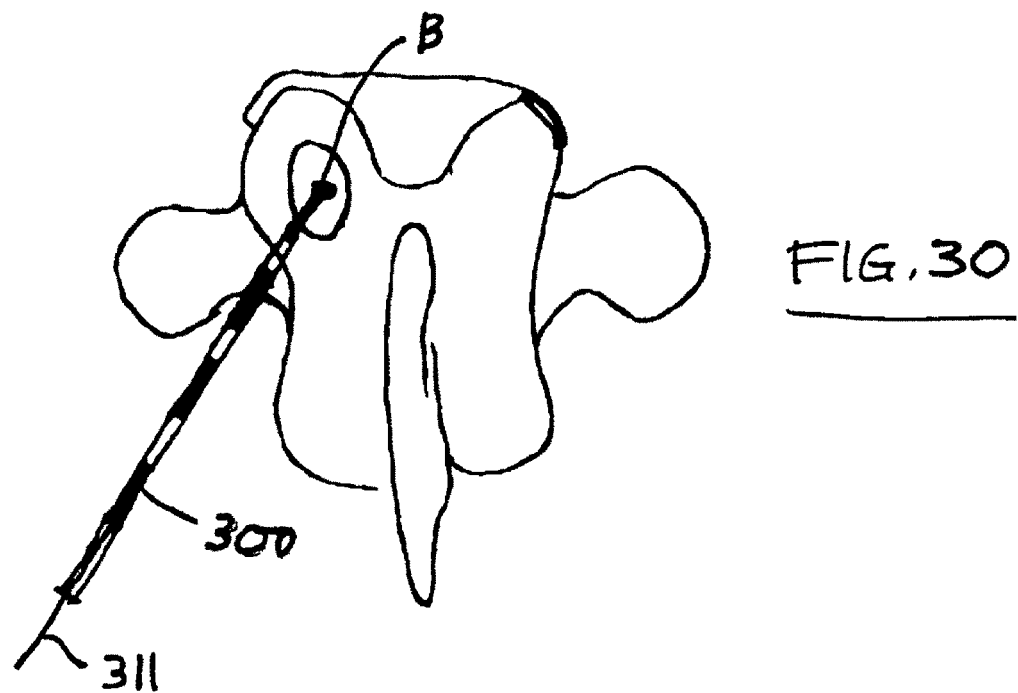
FIG. 30 is a schematic view similar to FIG. 29 wherein the awl/guide wire is partially inserted in the vertebra.
Figure 31:
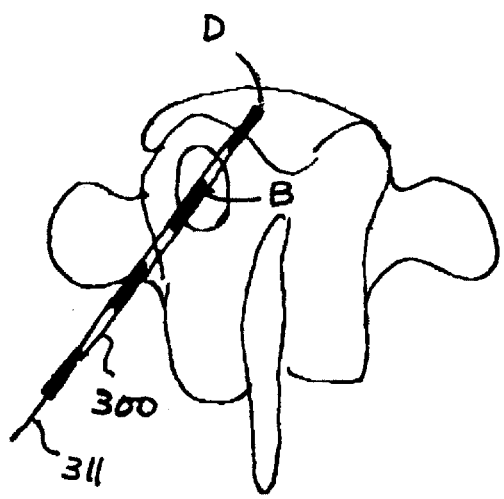
FIG. 31 is a schematic view similar to FIGS. 29 and 30, respectively, wherein the awl/guide wire is fully inserted in the vertebra.

A banded radioopaque/radiolucent and color banded awl/guide wire, such as 300/311 in FIG. 17b, is placed at point A as seen in FIG. 29 and advanced to point B as seen in FIG. 30. This demonstrates amount of penetration by measuring unit lengths seen in fluoroscopic imaging. Once the points A and B have been correctly identified then the banded awl/guide wire 300/311 is advanced to point D (FIG. 31).

Step 21

Figure 32:
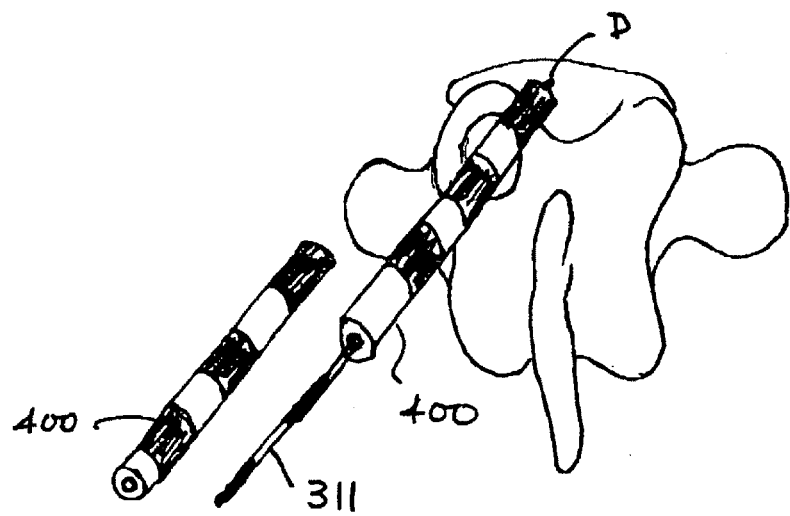
FIG. 32 is a schematic view similar to FIG. 31, wherein a drill bit is inserted in the vertebra over the guide wire.

A first cannulated, banded radioopaque/radiolucent and color banded drill bit 400 is then advanced over the guide wire 311 and drilled to depth point D. This is visualized under fluoroscopic imaging as seen in FIG. 32.

Step 22

Figure 33:
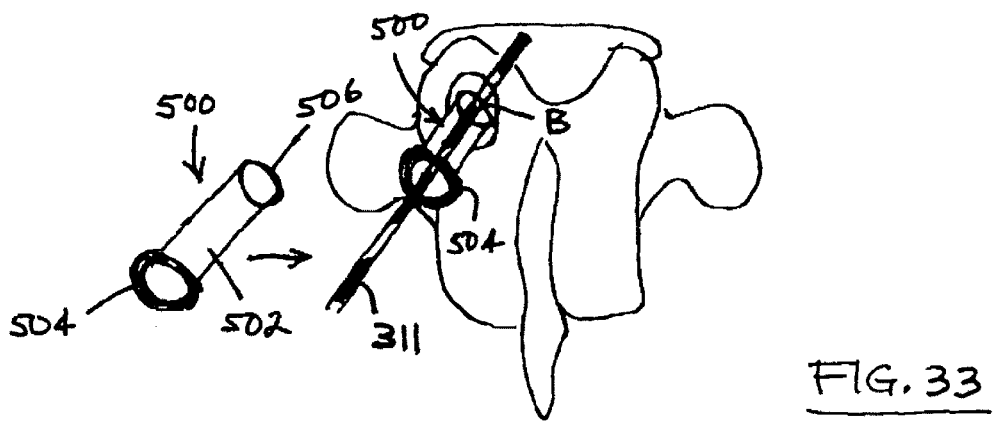
FIG. 33 is a schematic view similar to FIG. 31, wherein a first cannula is inserted in the vertebra over the guide wire.

In one embodiment, a first cannula 500 is then placed over the guide wire 311 and advanced into the pedicle flush with the posterior cortex. The cannula 500 has a radiolucent center 502, a radioopaque collar 504 which abuts against the posterior cortex and a radioopaque inner ring 506 corresponding to point B based on appropriate length measurements. It is tapped down securely to the posterior pedicle cortex surface as seen in FIG. 33. The guide wire 311 is then removed and a suitable instrument such as a catheter, cannula or needle is inserted through the first cannula into the interior of the pedicle for a desired procedure.

Step 23

Figure 34:
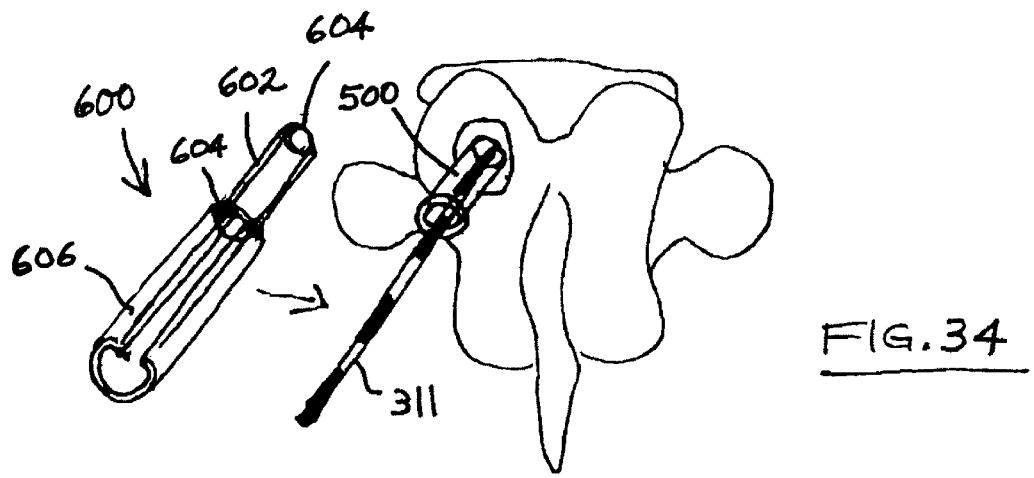
FIG. 34 is a schematic view similar to FIG. 33, showing the first cannula inserted in the vertebra and a second cannula to be inserted in the first cannula.
Figure 35:
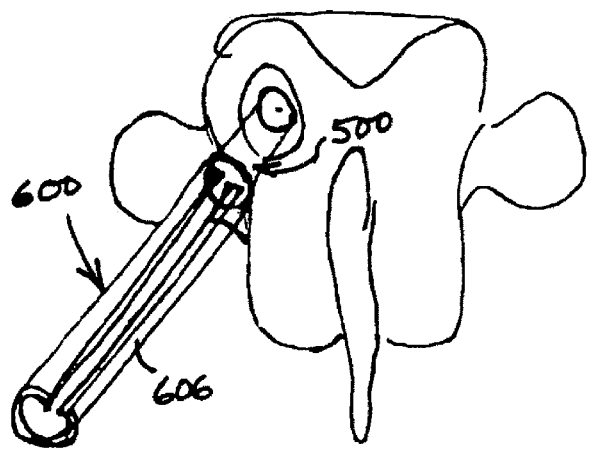
FIG. 35 is a schematic view similar to FIG. 34, wherein the second cannula is inserted in the first cannula.

In a second embodiment, a second hybrid cannula 600 (FIGS. 34, 35) is advanced into the first pedicle cannula 500. The second cannula 600 is comprised of a matching length radiolucent core inner section or cylinder 602 with radioopaque rings 604 on the ends thereof to correspond to the pedicle cannula 500. The second cannula also has an outer slotted cannula section 606 that extends beyond the skin for percutaneous applications. Furthermore, the second cannula has a suitable interlocking mechanism (not shown) with the first cannula 500 to facilitate appropriate placement with and removal of the first cannula as seen in FIG. 35. The interlocking mechanism may be a snap-fit, screw-fit or similar mechanism.

The banded guide wire 311 is then removed and the interlocked first cannula 500 and second specialized slotted cannula 600 function as a unit, working portal, for kyphoplasty, vertebroplasty or vertebral body biopsy instruments, as seen in FIG. 35. For pedicle screw placement a surgeon has a choice for placing screws in the manner described herein.

Step 24

In a third embodiment, the first cannula 500 may be omitted and the second cannula 600 may be inserted over the guide wire 311 directly within the opening created by the drill bit 400. The guide wire 311 is then removed and an appropriate instrument is inserted through the second cannula 600 into the pedicle for a desired procedure, in the manner shown in FIGS. 36-39.

Step 25

Figure 36:
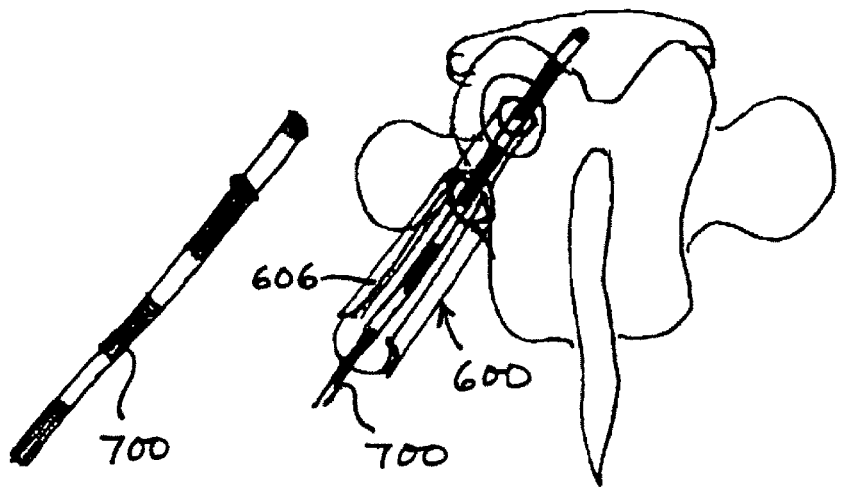
FIG. 36 is a schematic view similar to FIG. 35, showing a catheter or similar device is inserted in the vertebra through the second and/or first cannulas.

Access for the desired transpedicular procedure then proceeds along the traditional methods. An improvement of current equipment is a modified radioopaque/radiolucent and color banded kyphoplasty balloon catheter, vertebroplasty cannula or vertebral body biopsy needles 700 as seen in FIG. 36 for fluoroscopic imaging.

Step 26

For kyphoplasty procedures a balloon catheter 702 can be introduced straight and not bent into the first cannula 500 or into the slotted cannula 600, as seen in FIG. 37. The catheter 702 is advanced to the appropriate depth and inflated to proper pressure. Cement or other injected suitable material is then placed into the cavitary void created by the balloon catheter.

Step 27

An improvement over the current balloon catheter or similar instrument is not only the banding but also the provision of a fixed angled balloon catheter or instrument 704 as seen in FIGS. 38a-b and 39a-b. The slotted cannula 600 allows the introduction and advancement of the angled balloon catheter 704, which can come in prebent lengths or be manually bent to a desired angle based on the pedicle length A-B. Once the catheter 704 is fully abutted against the posterior pedicle cortex, it is further advanced into the vertebral body by simultaneously levering against the lateral aspect of the cannula 600 and forward pressure. This is visualized on fluoroscopic imaging as seen in FIGS. 39a and 39b. This new and improved method allows for more centralized placement of the catheter 704 within the vertebral body. When fully inserted in the vertebral body, the outer portion of the catheter 704 is received within the slotted cannula section 606. This has substantial advantages over a bilateral transpedicular approach, such as reduced operative time, decreased fluoroscopic imaging, the ability to combine with pedicle screw instrumentation for burst fractures, utilization in vertebral bodies with only one radio logically visible pedicle, and use in small volume vertebral bodies.

While many of the steps of the methods of the present invention are described as being computer-generated, it is noted that any suitable apparatus or device may be utilized to accomplish these steps in accordance with the methods of the present invention.

The invention has been described in connection with what is presently considered to be the most practical and preferred embodiments. It is to be understood that the invention is not to be limited to the disclosed embodiments, but on the contrary, is intended to cover various modifications and equivalent arrangements included within the spirit and scope of the appended claims.

What is claimed is:

1. A method for providing access to the interior of a pedicle for a desired transpedicular procedure, comprising:
inserting an awl with a separable guide wire in the pedicle at a predetermined starting point and in a predetermined trajectory to a desired depth, removing the awl from the pedicle and leaving the guide wire therein; positioning a cannulated drill bit over the guide wire and drilling an elongated opening in the pedicle inwardly to the desired depth; removing the drill bit from the opening and the guide wire; inserting a first cannula into the opening over the guide wire with an outer end of the first cannula flush with the adjacent portion of the posterior cortex of the pedicle; and removing the guide wire from the opening; whereby a kyphoplasty balloon catheter, vertebroplasty cannula or vertebral body biopsy needle may be inserted through the first cannula into the interior of the pedicle for the desired procedure;
wherein, before the guide wire is removed from the opening, a second cannula is partially inserted within the first cannula, the second cannula comprising an inner section that is slidabiy received within the first cannula and an enlarged outer section that extends outwardly from the first cannula, the outer section having a generally longitudinal slot extending therethrough from an inner end to an outer end thereof to enable instrument that is straight or angled to be inserted through the slot and through the first and second cannulas into the pedicle without requiring any relative movement between the inner section and the outer section.

2. The method of claim 1 wherein the awl and/or the guide wire and/or the drill bit are color banded for recognition of the position thereof and also are formed of radiolucent and radioopaque sections for fluoroscopic imaging.

3. The method of claim 1 wherein the first cannula is radiolucent and has a radioopaque collar at its outer end that engages the posterior cortex, and a radioopaque ring at its inner end.

4. The methods of claim 3 wherein an elongated instrument is inserted through the first cannula into the pedicle, the instrument being color banded for recognition of the position thereof and also having radioopaque and radiolucent sections for fluoroscopic imaging.

5. The method of claim 1 wherein the first and second cannulas are constructed to be interlocked when the second cannula is inserted in the first cannula.

6. The method of claim 1 wherein the first cannula is radiolucent and has a radioopaque collar at its outer end that engages the posterior cortex, and a radioopaque ring at the inner end thereof; and the inner section of the second cannula is radiolucent and has radioopaque rings on the inner and outer ends thereof that are aligned respectively with the radioopaque ring and radioopaque collar of the first cannula for fluoroscopic imaging.

7. A method for providing access to the interior of a pedicle for a desired transpedicular procedure, comprising:
inserting an awl with a separable guide wire in the pedicle at a predetermined starting point and in a predetermined trajectory to a desired depth;
removing the awl from the pedicle and leaving the guide wire therein;
positioning a cannulated drill bit over the guide wire and drilling an elongated opening in the pedicle inwardly to the desired depth;
removing the drill bit from the opening and the guide wire;
and inserting a cannula into the opening over the guide wire, the cannula comprising an inner section disposed in the opening and an enlarged outer section extending outwardly from the posterior cortex and having a generally longitudinal slot extending therethrough from an inner end to an outer end thereof to enable an instrument that is straight or angled to be inserted through the slot and through the cannula into the pedicle after the guide wire is removed without requiring any relative movement between the inner section and the outer section.

8. The method of claim 7 wherein the inner section of the second cannula is radiolucent and has radioopaque rings on the inner and outer ends thereof for fluoroscopic imaging.

* * * * *